(12) United States Patent
Adler et al.

(10) Patent No.: US 8,734,962 B2
(45) Date of Patent: May 27, 2014

(54) PHOSPHORESCENT METAL COMPLEX COMPOUND RADIATION EMITTING COMPONENT COMPRISING A PHOSPHORESCENT METAL COMPLEX COMPOUND AND METHOD FOR PRODUCTION OF A PHOSPHORESCENT METAL COMPLEX COMPOUND

(75) Inventors: Jürgen Adler, Kleinseebach (DE); Andreas Kanitz, Höchstadt (DE); Günter Schmid, Hemhofen (DE); Oksana Freydenzon, Nürnberg (DE); Anna Maltenberger, Leutenbach (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 838 days.

(21) Appl. No.: 12/601,520

(22) PCT Filed: May 20, 2008

(86) PCT No.: PCT/DE2008/000868
§ 371 (c)(1), (2), (4) Date: Apr. 20, 2010

(87) PCT Pub. No.: WO2008/141637
PCT Pub. Date: Nov. 27, 2008

(65) Prior Publication Data
US 2010/0213824 A1   Aug. 26, 2010

(30) Foreign Application Priority Data

May 21, 2007 (DE) .......................... 10 2007 023 554
May 22, 2007 (DE) .......................... 10 2007 023 749
Jan. 15, 2008 (DE) .......................... 10 2008 004 471
Jan. 25, 2008 (DE) .......................... 10 2008 006 113
Jan. 29, 2008 (DE) .......................... 10 2008 006 573
Mar. 27, 2008 (DE) .......................... 10 2008 015 940

(51) Int. Cl.
*C09K 11/06* (2006.01)
*H01L 51/54* (2006.01)

(52) U.S. Cl.
USPC ........... 428/690; 428/917; 313/504; 313/506; 252/301.16; 257/40; 257/E51.044; 548/103

(58) Field of Classification Search
USPC .................................. 548/103; 257/E51.044
See application file for complete search history.

(56) References Cited

U.S. PATENT DOCUMENTS

| | | | |
|---|---|---|---|
| 4,797,487 A | 1/1989 | A'Court | |
| 6,407,242 B1 | 6/2002 | Okuma | |
| 6,420,057 B1 | 7/2002 | Ueda et al. | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 7,063,901 B2 * | 6/2006 | Igarashi et al. | 428/690 |
| 2004/0065544 A1 | 4/2004 | Igarashi | |
| 2006/0099451 A1 | 5/2006 | Igarashi | |
| 2006/0154106 A1 | 7/2006 | Walters et al. | |
| 2006/0222887 A1 * | 10/2006 | Okada | 428/690 |
| 2006/0240282 A1 | 10/2006 | Lin | |
| 2006/0258043 A1 | 11/2006 | Bold et al. | |
| 2007/0048546 A1 | 3/2007 | Ren | |
| 2007/0111025 A1 | 5/2007 | Lennartz et al. | |
| 2008/0038586 A1 | 2/2008 | Nishizeki et al. | |
| 2008/0227979 A1 | 9/2008 | Saalbeck et al. | |
| 2009/0212280 A1 | 8/2009 | Werner et al. | |

FOREIGN PATENT DOCUMENTS

| | | | |
|---|---|---|---|
| CA | 2 549 309 | 9/2005 | |
| DE | 10 2004 010954 | 10/2005 | |
| DE | 10 2007 012 794 | 6/2008 | |
| EP | 0 198 680 | 10/1986 | |
| EP | 1 786 242 | 5/2007 | |
| JP | 10-226691 | 8/1998 | |
| JP | 11-116569 | 4/1999 | |
| JP | 11-158185 | 6/1999 | |
| JP | 2000-008033 A * | 1/2000 | C09K 11/06 |
| JP | 2000-229966 | 8/2000 | |
| JP | 2005-298483 A * | 10/2005 | C07F 15/00 |
| JP | 2007 084635 | 4/2007 | |
| JP | 2009-521110 | 5/2009 | |
| WO | WO 2005/019373 | 3/2005 | |
| WO | WO 2005/086251 | 9/2005 | |
| WO | WO 2005/097942 | 10/2005 | |
| WO | WO 2005/097943 | 10/2005 | |
| WO | WO 2006/008976 | 1/2006 | |
| WO | WO 2006/013738 | 2/2006 | |
| WO | WO 2006/098120 | 9/2006 | |
| WO | WO 2007/071450 | 6/2007 | |

OTHER PUBLICATIONS

Bailey et al., "A New Bridging Ligand lor the [Mo2]4+ Dimer: Syntheses and X-ray Crystal Strukturen of the Redox pair [Mo2[u-n2-(NPh)2CNHPh}4]0/+", Inorg. Chem. 1997, vol. 36, pp. 867-871 and correction vol. 36, No. 23, p. 5420, 1997.

Cotton et al., "Homologues of the Easily Ionized Compound Mo2(hpp)4 Containing Smaller Bicyclic Guanidinates", Inorganic Chemistry, 2006, vol. 45, pp. 5493-5500.

Cotton et al., "Strong Reducing Agents Containing Dimolybdenum MO2 4+ units and Their Oxidized Cations ith MO2 5+/6+ cores Stablized by bicyclic Guanidinate Anions with a Seven-Membered Ring", The Royal Society of Chemistry, Dalton Trans., 2006, pp. 4623-4631.

Berry et al., "A Hardwon Dirhodium Paddlewheel with Guanidinate Type (hpp) Bridging Ligands", Dalton Trans., 2005, vol. 23, pp. 3713-3715.

(Continued)

*Primary Examiner* — Michael H Wilson
(74) *Attorney, Agent, or Firm* — Cozen O'Connor

(57) ABSTRACT

A phosphorescent metal complex is provided, which comprises a metallic central atom M and at least one ligand coordinated by the metallic central atom M, wherein the one metallic central atom M and the ligand form a six-membered metallacyclic ring. Additionally specified are a radiation-emitting component comprising a metal complex, and a process for preparing the metal complex.

2 Claims, 9 Drawing Sheets

(56) References Cited

OTHER PUBLICATIONS

Clerac et al., "Completion of the Series of M2(hpp)4Cl2 Compounds from W to Pt: The W, Os and Pt Compounds", Inorg. Chem. 2000, vol. 39, pp. 2581-2584.

Mohamed et al., "Dinuclear and Tetranuclear Gold-Nitrogen Complexes. Solcent Influences on Oxidation and Nuclearity of Gold Guanidinate Derivatives", Inorg. Chem. 2007, vol. 46, pp. 11165-11172.

Cotton et al., "Closed-shell Molecules that Ionize More Readily than Cesium", Science vol. 298 (2002) pp. 1971-1974.

Cotton et al., "The Extraordinary Ability of Guanidinate Derivatives to Stabilize Higher Oxidation Numbers in Dimetal Units by Modification of Redox Potentials: Structures of Mo2 5+ and Mo2 6+ Compounds", Journal of American Chemical Society, vol. 124, 2002, pp. 9249-9256.

Ratilla et al: "Terminal and New Bridging Coordination of Methylguanidine, Arginine, and Canavanine to Platinum (II). The First Crystallographic Study of Bonding between a Transition Metal and a Guanidine Ligand", Inorg. Chem. vol. 29, No. 5, 1990, pp. 918-926.

Bailey et al: "Spectroscopic and Structural Properties of Binuclear Platinum-Terpyridine Complexes", Inorg. Chem. vol. 32, No. 4, Feb. 17, 1993, pp. 369-370.

Cotton et al: "Better Understanding of the Species with the Shortest Re26+ Bonds and Related Re27+ Species with Tetraguanidinate Paddlewheel Structures", Inorg. Chem. vol. 46, No. 5, 2007, pp. 1718-1726.

Cotton et al: "Paramagnetism at Ambient Temperature, Diamagnetism at Low Temperature in a Ru26+ Core: Structural Evidence for Zero-Field Splitting", Inorg. Chem. vol. 43, No. 26, 2004, pp. 8373-8378.

Ren et al., "A new class of o-hydroxyaryl-substituted N-heterocyclic carbine ligands and their complexes with palladium", Journal of Organometallic Chemistry, vol. 692, No. 10, pp. 2092-2098, Mar. 29, 2007.

K.S. Coleman et al., "Silver (I) complex of a new imino-N-heterocyclic carbene and ligand transfer to palladium (II) and rhodium (I)", Journal of the Chemical Society, Dalton Transactions, Chemical Society, pp. 2917-2922, Jun. 18, 2003.

M. Moser et al., "1,8-Bis (imidazolin-2-yliden-l-yl)carbazolide (bimca): A New CNC Pincer-Type Ligand with Strong Electron-Donating Properties, Facile Oxidative Addition of Methyl Iodine to Rh(bimca)(CO)", Organometallics, vol. 26, No. 4, pp. 1024-1030, Jan. 13, 2007.

A. J. Boydston et la., "Synthesis and Study of Bidentate Benzimidazolylidene-Group 10 Metal Complexes and Related Main-Chain Organometallic Polymers", Organometallics, vol. 25, No. 26, pp. 6087-6098, 2006.

B. E. Ketz et al., "Synthesis, structure, and olefin polymerization with nickel(II) N-heterocyclic carbene enolates", Chemical Communications, vol. 45, pp. 5693-5695, 2005.

B.E. Ketz et al., "Structure and Reactivity of an Allylpalladium N-Heterocyclic Carbene Enolate Complex", Organometallics, vol. 23, No. 12, pp. 2835-2837, 2004.

J. Brooks et al., "Synthesis and Characterization of Phosphorescent Cyclometalated Platinum Complexes", Inorganic Chemistry, vol. 41, No. 12, pp. 3055-3066, 2002.

F.A. Cotton et al., "Multiple Bonds between Atoms", pp. 1-21; Springerverlag, 2005.

\* cited by examiner

PHOSPHORESCENT METAL COMPLEX COMPOUND RADIATION EMITTING COMPONENT COMPRISING A PHOSPHORESCENT METAL COMPLEX COMPOUND AND METHOD FOR PRODUCTION OF A PHOSPHORESCENT METAL COMPLEX COMPOUND

RELATED APPLICATIONS

This is a U.S. national stage of application No. PCT/DE2008/000868, filed on May 20, 2008.

This application claims the priority of German application nos. 10 2007 023 554.4 filed May 21, 2007, 10 2007 023 749.0 filed May 22, 2007, 10 2008 004 471.7 filed Jan. 15, 2008, 10 2008 006 113.1 filed Jan. 25, 2008, 10 2008 006 573.0 filed Jan. 29, 2008 and 10 2008 015 940.9 filed Mar. 27, 2008, the disclosure content of all of which is hereby incorporated by reference.

The invention relates to a phosphorescent metal complex, to a radiation-emitting component which comprises the phosphorescent metal complex, and to a process for preparing the phosphorescent metal complex.

BACKGROUND OF THE INVENTION

For radiation-emitting components, for example organic light-emitting diodes (OLEDs), organic materials which emit colored light are used. To date, there is a multitude of materials which emit red or green light. However, existing methods have been unable to prepare stable materials which emit deep blue, light blue or blue-green light.

SUMMARY OF THE INVENTION

It is an object of the invention to provide a novel phosphorescent compound which can emit colored, for example deep blue, light blue, blue-green or green light and is stable. A further object is to provide a radiation-emitting component which comprises such a phosphorescent compound. The preparation of a phosphorescent compound is a further object of the invention.

These and other objects are attained in accordance with one aspect of the present invention directed to a phosphorescent metal complex which comprises at least one metallic central atom M and at least one ligand coordinated by the metallic central atom M is provided, wherein the one metallic central atom M and the ligand form a six-membered metallacyclic ring. This provides a stable complex which can emit colored light, for example in the deep blue, light blue, blue-green or green range.

The metallacyclic ring may comprise at least two heteroatoms. In addition, the central atom of the metallacyclic ring is coordinated or bonded to at least one atom of the ligand which has a free electron pair, for example to a nitrogen atom or to the carbon atom of a carbene.

In addition, the ligand which forms a six-membered metallacyclic ring with the metallic central atom M may have a tautomerizable unit in the uncoordinated state. The tautomerizable unit may extend over one or more, for example two, ring systems that the ligand comprises. In the coordinated state, the ligand may have mesomerism, which brings about delocalization of the electrons in the six-membered metallacyclic ring.

Formulae 1 and 2 show examples of tautomerizable ligands. Charge redistribution changes the alternating charge distribution, while a substituent (H) of the methylene group (formula 1) or of the NH group (formula 2) moves to a nitrogen atom of an aromatic ring.

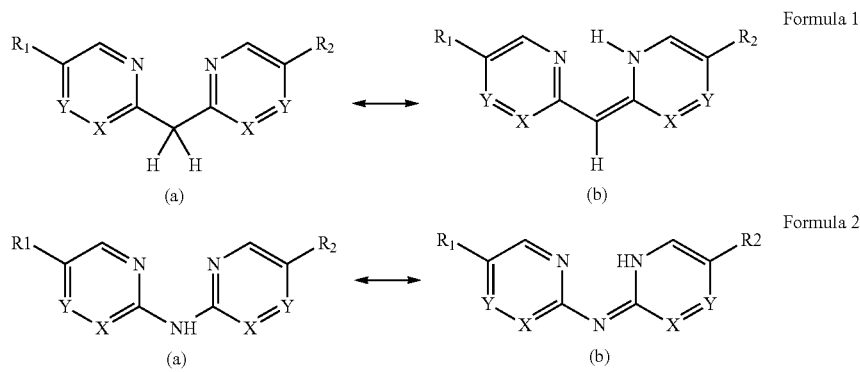

For X and Y, it is possible here to use, for example, C—H or N; $R_1$ and $R_2$ in this example can be selected freely.

The structural formulae shown in the formulae 1 and 2 in each case constitute merely examples for illustrating the tautomerizability of ligands.

The tautomerizable units in the ligands enable coordination to a metallic central atom M to form a six-membered metallacyclic ring, in the course of which a proton of the ligand is eliminated.

The metallic central atom M may be selected from a group which comprises Ir, Pt, Au, Re, Rh, Ru, Os, Pd, Ag, Zn, Al and lanthanoids, for example Eu. The group may also include metals or transition metals with an atomic number of >35.

In a further embodiment, the phosphorescent metal complex has the structural formula as shown in formula 3,

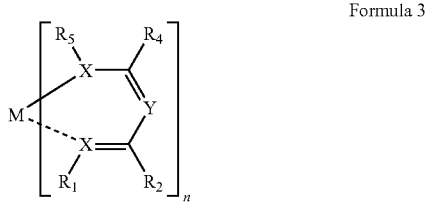

where:
n=1 to 3,
Y=C—H, N, P, As, Sb, C—$R_y$, Si—$R_y$, Ge—$R_y$,
X=N, O, P, As, Sb, $R_1$, $R_2$, $R_y$, $R_4$ and $R_5$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN, $R_1$ and $R_5$ include a free electron pair when X is O.

In the case that X=O, the double bond X=C in formula 3 is considered to be part of a delocalized electron system, and the $R_1$ and $R_2$ radicals are configured such that O is involved in a 6π-electron system. This applies analogously to the following formulae when X=O.

For example, n=1 or 2 when M=Pt, n=1 when M=Au, and n=1, 2 or 3 when M=Ir (also applies to the compounds depicted hereinafter). The number of the ligands with which the central atom forms a six-membered metallacyclic ring depends on how many further ligands are coordinated to the central atom. When M=Au, it is also possible for Au—Au interactions to occur, which lead, for example, to bridge formation between metal complexes.

The formula 3 and the following formulae showing a metal complex show only the ligand(s) which form(s) a six-membered metallacyclic ring with the central atom. The complete formula 3 and the formulae which follow are $L_mM[\ ]_n$ where n=1 to 3, m=3−n, [ ]=ligands which form a six-membered metallacyclic ring with the central atom, and L=one ligand which forms a five-membered ring with the central atom or two ligands which coordinate to the central atom in a monodentate manner. The number of all ligands may, for example, be sufficiently high that the central atom has a coordination sphere in which the 18-electron rule is satisfied for the central atom.

Among all ligands of the formula 3 which form a six-membered metallacyclic ring with the central atom, at least one ligand which is not acetylacetonate is present, i.e. one ligand in which the following is not true simultaneously: X=O for both X, $R_2$ and $R_4$=$CH_3$, $R_1$ and $R_5$ are each a free electron pair and Y=CH.

"Substituted" is understood here and hereinafter such that the particular groups have one or more substituents, the substituents being freely selectable and being selected, for example, from a group comprising H, halogens and alkyl radicals.

Alkyl radicals here and hereinafter may comprise, for example, one to 20 carbon atoms.

Formula 4

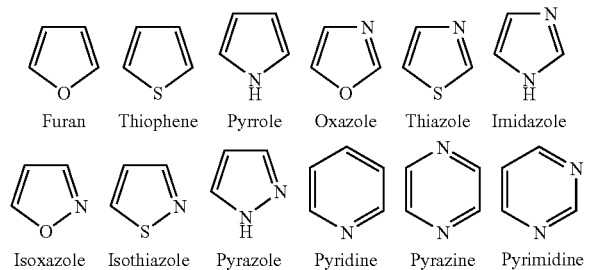

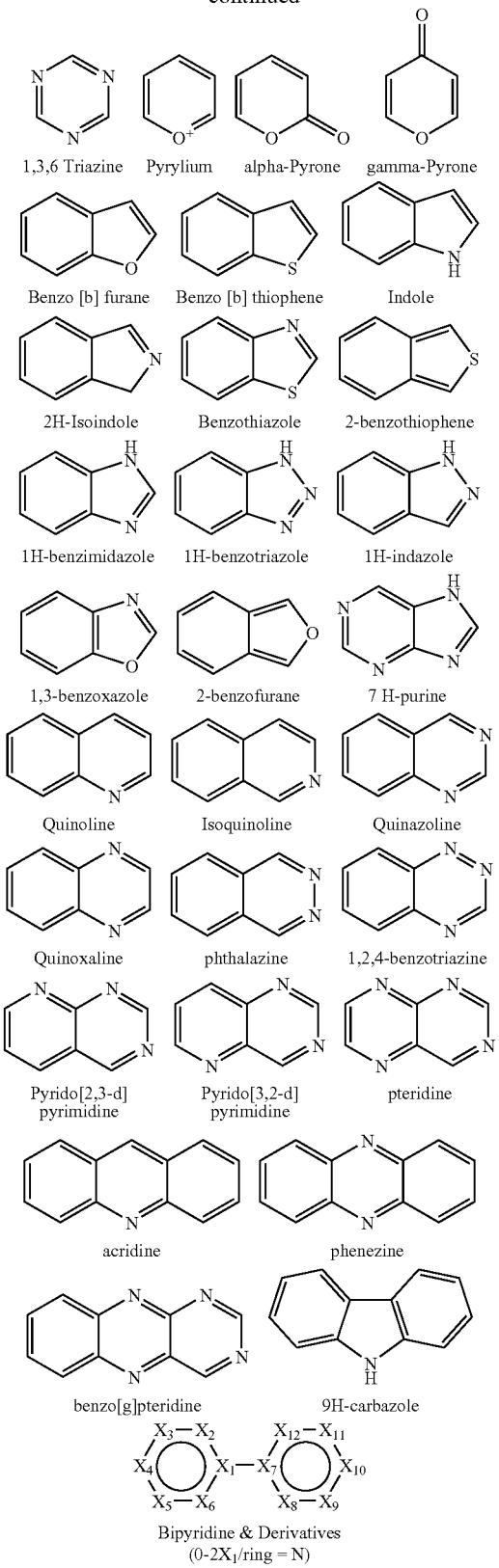

A selection of examples of heterocycles which can be used for $R_1$, $R_2$, $R_y$, $R_4$ and $R_5$ is given in formula 4, in each case showing base structures which may in turn have substituents.

These illustrative $R_1$, $R_2$, $R_y$, $R_4$ and $R_5$ may each be bonded to the ligand at any desired bondable position in the base structure.

Formula 5 shows an illustrative structural formula for $Y=C-R_y$ (a) or $Y=Si-R_y$ (b):

Formula 5

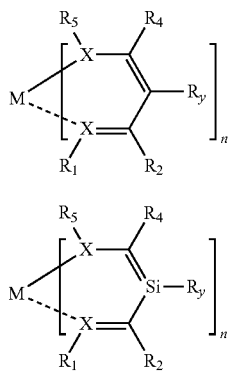

In addition, the $R_1$ and/or $R_5$ radicals shown in the formulae 3 and 5 may additionally be coordinated to the metallic central atom M. This further stabilizes the compound. The ligand(s) on the central atom M may have an acceptor effect and hence lead to shorter wavelengths of the light emitted by the compound. The emission of colored, for example deep blue, light blue, blue-green or green light is thus enabled.

In a further embodiment, at least one of $R_1$ and $R_2$, $R_2$ and $R_y$, $R_y$ and $R_4$, $R_4$ and $R_5$ may be bridged to one another. The bridges may each occur independently. Formula 6 shows a schematic of bridges B1, B2, B3 and B4 on the ligand.

Formula 6

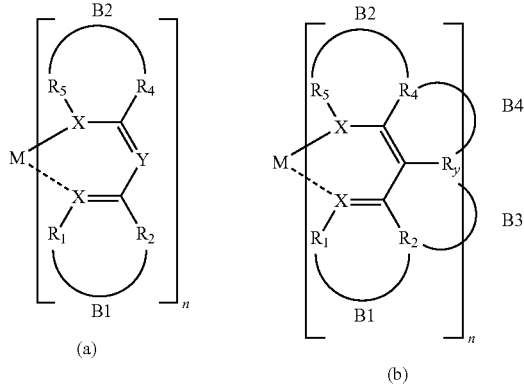

The compound may be selected from a structural formula of the formula 7 where:
n=1 to 3,
$Y=C-H$, N, P, As, Sb, $C-R_y$, $Si-R_y$, $Ge-R_y$,
X=N, O, P, As, Sb,
$X_1$, $X_2$, $X_3$, $X_4$, $X_5$, $X_6$, $X_7$ and $X_8$ are each independently C or—when $R_{11}$, $R_{12}$, $R_3$, $R_{14}$, $R_{15}$, $R_6$, $R_7$ or $R_8$ includes a free electron pair —N,
$R_y$, $R_{11}$, $R_{12}$, $R_3$, $R_{14}$, $R_{15}$, $R_6$, $R_7$ and $R_8$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

Formula 7

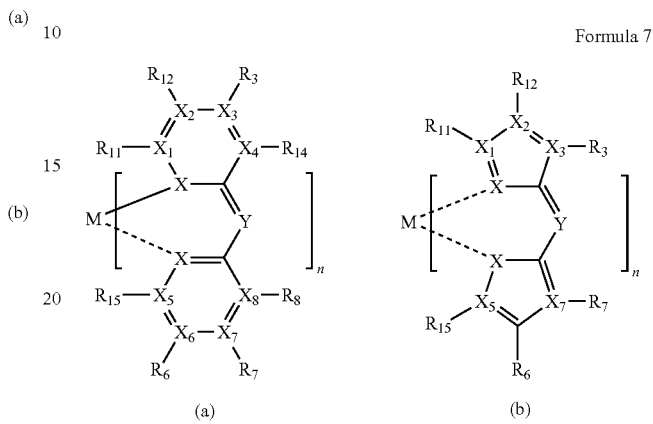

The bridges can achieve additional stability of the metal complex and a shift of the wavelength of the light emitted, for example into the shorter-wave range.

The compound of the formula 7 may also have a symmetric shape where $X_1=X_5$, $R_{11}=R_{15}$, $X_2=X_6$, $R_{12}=R_6$, $X_3=X_7$, $R_3=R_7$, $X_4=X_8$ and $R_{14}=R_8$.

Compounds according to the structural formula in formula 7a can be derived, for example, from bis-pyridine derivatives. In that case, for example, it is possible that X=N and $X_1=X_2=X_3=X_4=X_5=X_6=X_7=X_8=C$. The $R_{11}$, $R_{12}$, $R_3$, $R_{14}$, $R_{15}$, $R_6$, $R_7$ and $R_8$ radicals may be selected freely from the above-mentioned options. For $R_6$ and $R_{12}$, it is then possible, for example, to use electron-withdrawing substituents which are selected from a group comprising CN, F, 4-pyridyl, triazyl, 2-pyrimidyl, 5-pyrimidyl, 2-oxazole, 4-oxazole, 2-thiazolyl, 4-thiazole, trifluoromethyl and hexafluoroisopropylidene.

A further example of a compound of the structural formula in formula 7a is derived from bispyrazine derivatives, and results from X=N, $X_1=X_2=X_4=X_5=X_6=X_8=C$ and $X_3=X_7=N$. $R_3$ and $R_7$ are each a free electron pair.

Compounds which derive from bispyrimidine derivatives result from X=N, $X_1=X_2=X_3=X_5=X_6=X_7=C$ and $X_4=X_8=N$, where $R_4$ and $R_8$ are each a free electron pair. For $R_6$ and $R_{12}$, it is then possible to use, for example, electron-withdrawing substituents which are selected from a group comprising CN, F, 4-pyridyl, triazyl, 2-pyrimidyl, 5-pyrimidyl, 2-oxazole, 4-oxazole, 2-thiazolyl, 4-thiazole, trifluoromethyl and hexafluoroisopropylidene.

Compounds of the formula 7a may result from bistriazine derivatives. In that case, X=N, $X_2=X_3=X_5=X_7=C$, $X_1=X_4=X_6=X_8=N$, where $R_1$, $R_4$, $R_6$ and $R_8$ are each a free electron pair. For $R_3$ and $R_7$, it is then possible to use, for example, electron-withdrawing substituents which are selected from a group comprising CN, F, 4-pyridyl, triazyl, 2-pyrimidyl, 5-pyrimidyl, 2-oxazole, 4-oxazole, 2-thiazolyl, 4-thiazole, trifluoromethyl and hexafluoroisopropylidene. Alternatively, the nitrogen positions can be permuted, such that X=N, $X_1=X_3=X_5=X_7=C$, $X_2=X_4=X_6=X_8=N$, where $R_2$, $R_4$, $R_6$ and $R_8$ are each a free electron pair, or X=N, $X_1=X_2=X_5=X_6=C$, $X_3=X_4=X_7=X_8=N$, where $R_3$, $R_4$, $R_7$ and $R_8$ are each a free electron pair.

A compound of the structural formula in formula 7b can be derived, for example, from bispyrrole derivatives, by setting $X=N$, $X_1=X_2=X_3=X_5=X_6=X_7=C$. For $R_{11}$ and $R_{15}$, it is then possible, for example, to use electron-withdrawing substituents which are selected from a group comprising CN, F, 4-pyridyl, triazyl, 2-pyrimidyl, 5-pyrimidyl, 2-oxazole, 4-oxazole, 2-thiazolyl, 4-thiazole, trifluoromethyl and hexa-fluoroisopropylidene.

The $R_{11}$ and $R_{12}$, $R_{12}$ and $R_3$, $R_3$ and $R_{14}$, $R_{14}$ and $R_y$, $R_y$ and $R_8$, $R_{15}$ and $R_6$, $R_6$ and $R_7$ or $R_7$ and $R_8$ radicals may also each independently form further bridges. It is thus possible to provide fused systems in the ligand.

For example, such fused systems may have a structural formula of the formulae 8a, 8b and 8c, where each of the $X_1$ to $X_{12}$ positions may each independently be N or C—R, and R is selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. R may be different for each X.

Formula 8

(a)

(b)

(c)
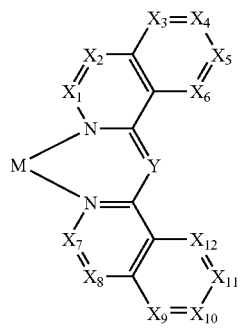

In formula 8, for reasons of clarity, n is set to 1 and only one ligand coordinates to the metallic central atom M. According to the type of central atom M, however, it is also possible for further ligands which form a six-membered metallacyclic ring with the central atom to be present in the compound.

Further examples of compounds with fused systems are shown in formula 9. The formulae 9a to d show examples of compounds on which fused-on oxazole rings are present. The formulae 9e to g show examples of more highly fused systems. The $R_5$ and $R_6$ radicals in the compounds of the formulae 9a to 9d in this case may each independently be selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. The $X_1$ to $X_4$ positions may be selected analogously to formula 8.

Formula 9 shows examples of five-membered rings which are fused to aromatic six-membered rings incorporated into the metallacyclic ring in the ligand. In a further embodiment, six-membered rings which are fused to aromatic five-membered rings incorporated into the metallacyclic ring are possible in the ligands.

Formula 9

(a)

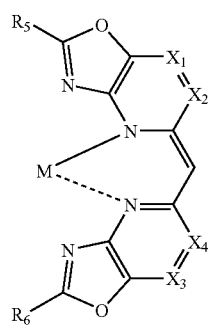

(b)

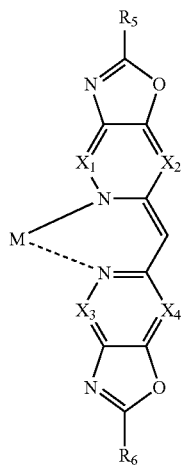

(c)

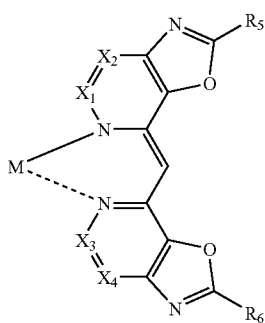

(d)

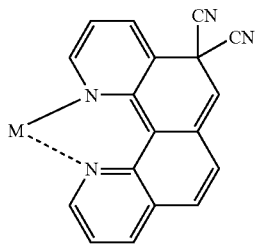

(e)

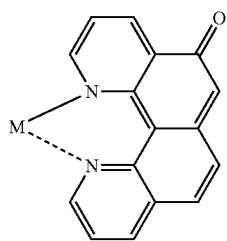

(f)

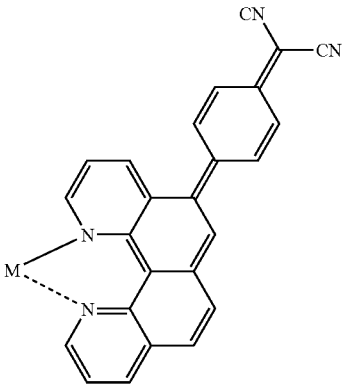

(g)

In a further embodiment, the compound may have a structural formula of the formula 10, where:

n=1 to 3,
Y=C—H, N, P, As, Sb, C—$R_y$, Si—$R_y$, Ge—$R_y$,
X=N, O, P, As, Sb,
$X_1$, $X_2$, $X_5$ and $X_6$ are each independently C or—when $R_{11}$, $R_{12}$, $R_{15}$ or $R_6$ is a free electron pair —N,
$X_3$ and $X_7$ are each S,
$R_y$, $R_{11}$, $R_{12}$, $R_{15}$ and $R_6$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

Formula 10

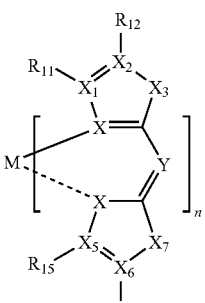

(b)

For example, a compound of the formula 10 can be derived from bisthiazole derivatives by using $X_1=X_2=X_5=X_6=C$, X=N and $X_3=X_7=S$. For $R_{11}$ and $R_{15}$, it is then possible, for example, to use electron-withdrawing substituents which are selected from a group comprising CN, F, 4-pyridyl, triazyl, 2-pyrimidyl, 5-pyrimidyl, 2-oxazole, 4-oxazole, 2-thiazolyl, 4-thiazole, tri-fluoromethyl and hexafluoroisopropylidene.

In compounds of the formula 10, it is additionally possible to set $X_1=X_5$, $R_{11}=R_{15}$, $X_2=X_6$, $R_{12}=R_6$ and $X_3=X_7$. Symmetric ligands are thus obtained. The $R_{11}$ and $R_{12}$ and/or $R_{15}$ and $R_6$ radicals may also be bridged to one another, which leads to a further increase in the stability of the compound.

Both the compounds of the formula 10 and those of the formulae 7 to 9 have an azadiketone-like or diketone-like structure, which contributes to the stability of the ligand and the colored emission with, for example, a deep blue, light blue, blue-green or green emission color of the compound.

In a further embodiment, the compound may have a structural formula which is selected from a group comprising the structural formulae of the formula 11, where:

n=1 to 3,

Y=C—H, N, P, As, Sb, C—$R_y$, Si—$R_y$, Ge—$R_y$, $X_1$, $X_2$, $X_3$ and $X_4$ are each independently C—R or N, $R_y$ and R are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. R may be selected differently for each X.

Formula 11

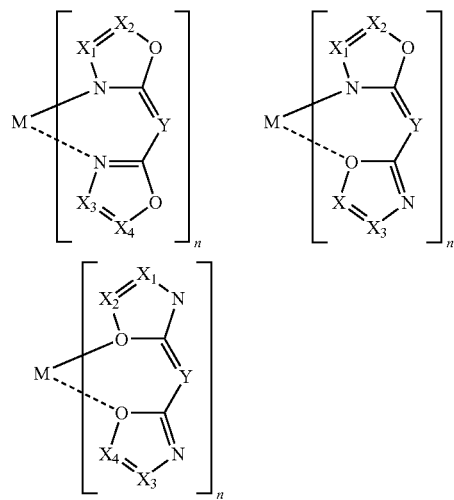

These compounds have a diketone-like structure in five-membered aromatic rings. Further five-membered aromatic rings in the ligand, for example thiazoles, phosphazoles or imidazoles, are also conceivable.

Additionally provided is a radiation-emitting component which comprises a substrate, at least one lower, first electrode layer on the substrate, at least one organic emitting layer on the first electrode layer, and an upper, second electrode layer, wherein at least one metal complex in which at least one central atom M is involved in at least one six-membered metallacycle is embedded in a matrix in the emitting layer. In this case, the substrate and the first electrode layer may be transparent and the central atom M may be coordinated to at least one ligand, the central atom and the ligand being selected according to the statements made above.

In a further embodiment, the phosphorescent metal complex has a structural formula of the formula 12, where:

Formula 12

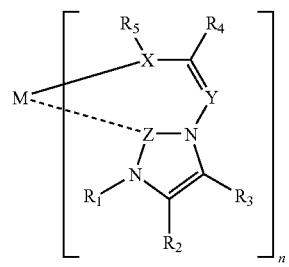

n=1 to 3,

Y=C—H, N, P, As, Sb, C—$R_y$, Si—$R_y$, Ge—$R_y$,

X=N, O, P, As, Sb,

Z=C, Si, Ge, $R_1$, $R_2$, $R_3$, $R_y$, $R_4$ and $R_5$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. For example, the $R_1$, $R_2$, $R_3$, $R_y$, $R_4$ and $R_5$ radicals may be selected from a group comprising the structural formulae of the formula 4.

The ligand of the metal complex may comprise a carbene ligand. The carbene ligand is coordinated to the central atom via a carbon atom and a heteroatom such that the carbene structural unit is involved in the six-membered metallacyclic ring.

The compound of the formula 12 has a high stability and lifetime. In addition, such a compound can emit radiation of a wavelength which is within the visible range and gives, for example, deep blue, light blue, blue-green or green light. In addition, the polarity in such a compound is reversed compared to five-membered metallacyclic compounds, since the heteroatom, for example a nitrogen atom, is incorporated in anionic form, and the Z atom, for example C, in uncharged form into the six-membered metallacycle.

The two $R_1$ and $R_5$ radicals in formula 12 may additionally be coordinated to the central atom M. In addition, at least one of $R_1$ and $R_2$, $R_2$ and $R_3$, $R_3$ and $R_y$, $R_y$ and $R_4$, and $R_4$ and $R_5$ may be bridged to one another. A schematic bridging of the radicals is shown in formula 13. The individual bridges $B_{45}$, $B_{23}$, $B_{4y}$ and $B_{3y}$ may each be present independently.

Formula 13

(a)

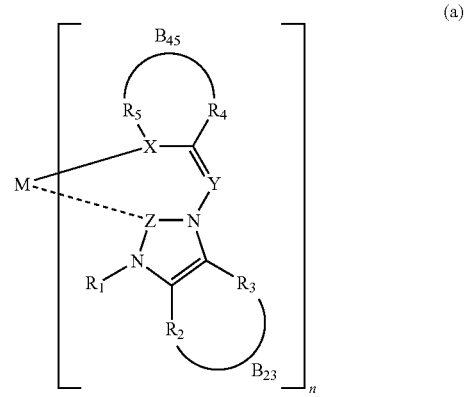

-continued

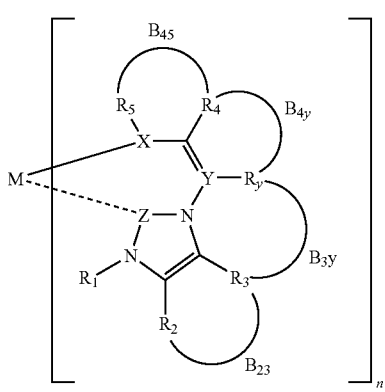

(b)

For the definitions of X, Y, Z, $R_1$ to $R_5$ and n in formula 13, the options shown for the structural formula shown in formula 12 apply analogously.

In addition, the compound may have a structural formula of the formula 14, where:
n=1 to 3,
Y=C—H, N, P, As, Sb, C—$R_y$, Si—$R_y$, Ge—$R_y$,
X=N, O, P, As, Sb,
Z=C, Si, Ge,
$X_5$, $X_6$, $X_7$ and $X_8$ are each independently C—R or—when $R_{15}$, $R_6$, $R_7$ or $R_8$ includes a free electron pair —N,
$Z_1$, $Z_2$, $Z_3$ and $Z_4$ are each C—$R_z$, where $R_z$ may be different for each Z,
R, $R_z$, $R_1$, $R_2$, $R_3$, $R_y$, $R_4$, $R_5$, $R_{15}$, $R_6$, $R_7$ and $R_8$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

Formula 14

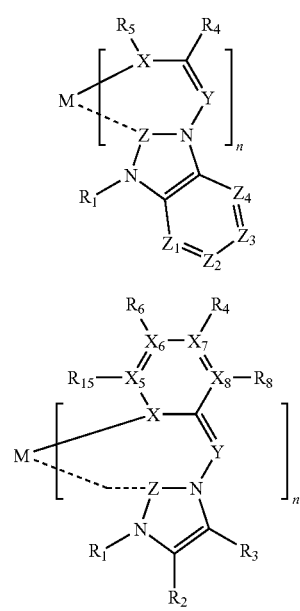

For example, X=N and Y=C—$R_y$ can be used here.

The $R_1$ and $R_2$, $R_2$ and $R_3$, $R_5$ and $R_4$, $R_4$ and $R_y$, $R_{15}$ and $R_6$, $R_6$ and $R_7$, $R_7$ and $R_8$, $R_8$ and $R_y$ or $R_y$ and $R_3$ radicals may each independently be bridged to one another.

The structure shown in formula 14a may, for example, be a carbene derivative which derives from benzimidazole. In that case, Z=C, Y=C—$R_y$, X=N and $Z_1$=$Z_2$=$Z_3$=$Z_4$=C—$R_z$.

In the formulae 14a and 14b, it is possible to set Z=C, Y=N or Y=C—$R_y$. Whereas there is an aromatic bridge of the carbene with the six-membered ring via an N—C=C— structural unit when Y=C—$R_y$, there is an aromatic bridge via an N—C=N structural unit when Y=N.

Compounds which have a bridge may be derived, for example, from pyridine derivatives. In that case, in the compound of the formula 14b, Z=C, Y=N, $X_5$=$X_6$=$X_7$=$X_8$=C. $R_7$ can be selected, for example, such that it has an electron-withdrawing effect, such as $R_7$=CN, F, 4-pyridyl, triazyl, 2-pyrimidyl, 5-pyrimidyl, 2-oxazolyl, 4-oxazolyl, 2-thiazolyl, 4-thiazolyl, tri-fluoromethyl or hexafluoroisopropylidene.

When the compound of the formula 14b is derived from pyrazine derivatives, Z=C, Y=N, $X_5$=$X_6$=$X_8$=C, $X_7$=N and $R_7$ is a free electron pair.

Pyrimidine-derived compounds of the formula 14b result from Z=C, Y=N, $X_5$=$X_6$=$X_7$=C, $X_8$=N and $R_8$ is a free electron pair. $R_7$ may, for example, be electron-withdrawing and be selected from CN, F, 4-pyridyl, triazyl, 2-pyrimidyl, 5-pyrimidyl, 2-oxazolyl, 4-oxazolyl, 2-thiazolyl, 4-thiazolyl, tri-fluoromethyl or hexafluoroisopropylidene.

Compounds of the formula 14b which are derived from triazine result from Z=C, Y=N, $X_6$=$X_7$=C, $X_5$=$X_8$=N, where $R_5$ and $R_8$ are each a free electron pair. $R_7$ can be selected here to be electron-withdrawing (see above). Permutation of the nitrogen positions can provide further triazine derivatives, for example $X_5$=$X_6$=C, $X_7$=$X_8$=N, where $R_7$ and $R_8$ are each a free electron pair and $X_5$=$X_7$=C, $X_6$=$X_8$=N, where $R_6$ and $R_8$ are each a free electron pair. $R_5$ and $R_7$ can then be selected to be electron-withdrawing.

Examples of fused systems in the ligand are shown in the formulae 15 and 16. Examples are given here for carbenes (Z=C); analogous structures of silylenes (Z=Si) or germylenes (Z=Ge) are equally conceivable. For each $X_1$ to $X_6$, C—R or N can be used there, where R may be different for each X, and R and $R_{25}$ are each independently selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. Further fused systems which are not shown here may likewise be present.

Formula 15

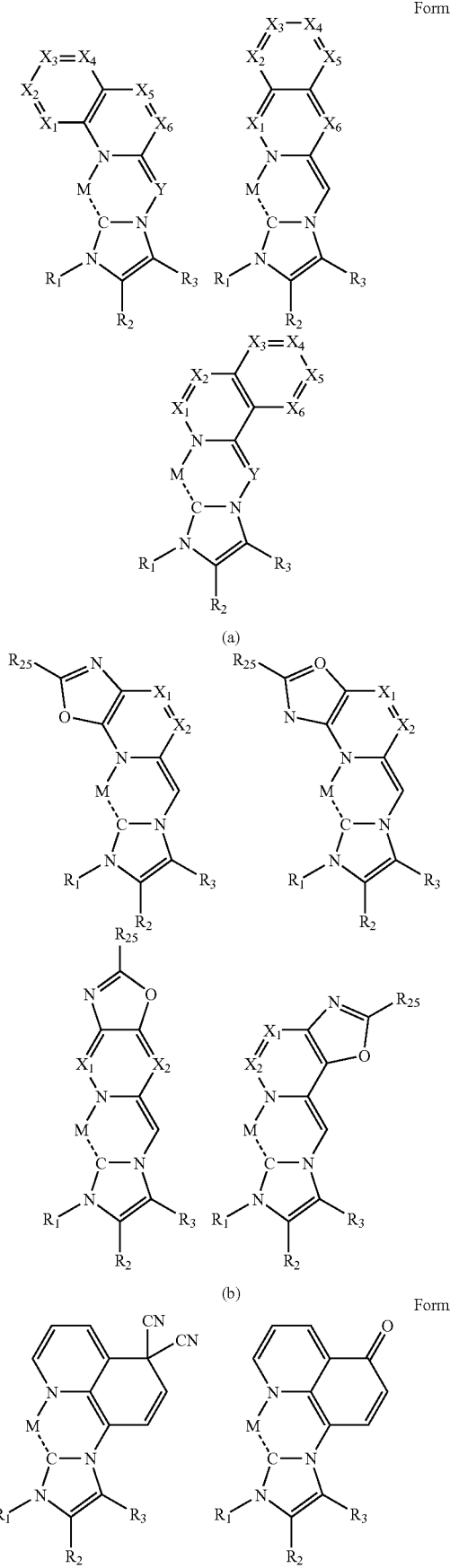

(a)

(b)

Formula 16

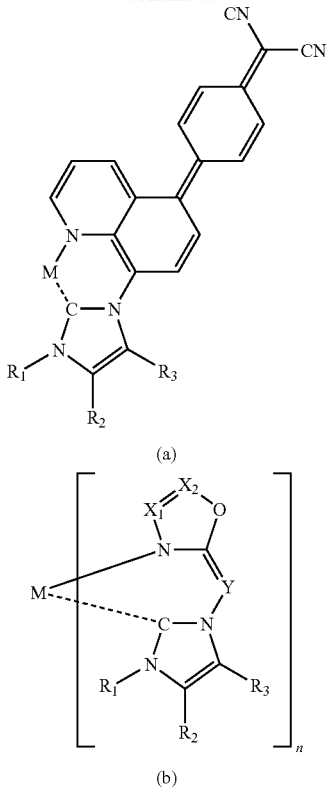

(a)

(b)

Formula 15a shows compounds with six-membered fused systems in the carbene ligand. Formula 15b shows five-membered fused systems using the example of oxazole derivatives in the carbene ligand.

Formula 16a shows examples of more highly fused systems. For the sake of clarity, formulae 15 and 16a each show only one ligand coordinated to the central atom. However, it is also possible, according to the selection of the central atom, for a plurality of ligands to be present.

A compound with a carbene ligand which has an electron-withdrawing structure is shown in formula 16b, where $X_1$, $X_2$, Y, n, $R_1$, $R_2$ and $R_3$ may be selected analogously to the compound in formula 14 (where $X_1$ and $X_2$ correspond to the $X_5$, $X_6$ and $X_7$ shown there).

In addition, a radiation-emitting component is provided, which comprises a substrate, at least one lower, first electrode layer, at least one organic emitting layer and above that at least one upper, second electrode layer, wherein a metal complex which has at least one metallic central atom M which is part of a six-membered metallacyclic ring, where at least one carbene ligand is incorporated directly in the metallacyclic ring, is embedded in a matrix in the emitting layer. In this case, the substrate and the first electrode layer may be configured to be transparent.

In a further embodiment, the tautomerizable unit may have the structural unit —C(H,R)— or —N(H)—, and connect an electron-deficient and an electron-rich aromatic.

The terms "electron-deficient" and "electron-rich" are used in such a way that an aromatic ring system is modified by substituents and/or replacement of carbon atoms which are part of the ring system with heteroatoms such that they have a reduced (electron-deficient) or increased (electron-rich) electron density in the ring system compared to the unsubstituted and/or unreplaced systems, for example benzene.

In a further embodiment, a compound which has a structural formula of the formula 17

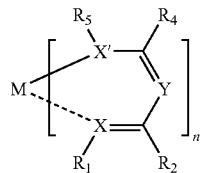

Formula 17 is provided, where:

n=1 to 3,

Y=C—H, N, P, As, Sb, C—R$_y$, Si—R$_y$, Ge—R$_y$,

X and X' are each independently N, O, P, As or Sb,

R$_1$, R$_2$, R$_4$, R$_5$ and R$_y$ are each independently selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN, and R$_1$ together with R$_2$ and C=X, and R$_4$ together with R$_5$ and C—X', form at least one aromatic ring each. The R$_1$ to R$_5$ and R$_y$ radicals may, for example, comprise one of the structural formulae of the formula 4.

Formula 17 indicates only one mesomeric form of the ligand coordinated to the central atom. When another mesomeric form is present, the ligand may also comprise a C=X' unit and a C—X unit, each of which forms aromatic rings with the corresponding radicals.

Such a compound is oxidation- and reduction-stable by virtue of the specific selection of the ligand and has a high lifetime as a result.

The aromatic ring can be selected from a structural formula which is selected from a group which comprises structural formulae of the formula 18.

Formula 18

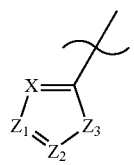

(a)

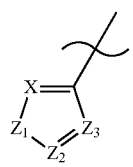

(b)

-continued

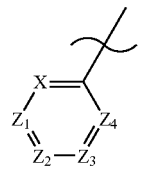

(c)

In these formulae: X=X' and is selected from N, O, P, As or Sb,

Z$_1$, Z$_2$, Z$_3$ and Z$_4$ are each independently divalent or trivalent and are selected from C—R, N when Z$_1$, Z$_2$, Z$_3$ and Z$_4$ are trivalent, and from O, S, N—R, Se when Z$_1$, Z$_2$, Z$_3$ and Z$_4$ are divalent, R is, for each Z, selected independently from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

In addition, one of the aromatic ring formed from R$_5$, R$_4$ and C=X and the aromatic ring formed from R$_1$, R$_2$ and C—X' may be electron-rich, and the other aromatic ring in each case electron-deficient.

This can be achieved, for example, by the combination of a five-membered ring and of a six-membered ring in the ligand. Five-membered aromatic systems, for example pyrroles, imidazoles, furans, thiophenes, dithiols and thiazoles, are electron-rich and readily obtainable. Likewise electron-rich are non-heterocyclic six-membered aromatic rings which are substituted by substituents such as alkoxy or amine groups, for example. Electron-rich systems may be suitable as hole conductors.

Electron-deficient systems, which may be suitable as electron conductors, are, for example, six-membered heterocyclic aromatic systems such as pyridine, pyrimidine or pyrazine. Benzene derivatives or five-membered aromatic systems may become electron-deficient as a result of fluorination or nitration.

When an electron-deficient aromatic and an electron-rich aromatic are combined with one another in a ligand via a tautomerizable unit, for example the structural units —C—(H,R)— or —N(H)—, stable tautomerizable ligands are obtained, which coordinate to a metallic central atom M with elimination of a proton to form a stable six-membered metallacyclic ring. Owing to the specific ligand, this compound is stable to reduction and oxidation, since both a high hole concentration and a high electron concentration can be compensated for by the ligand.

Formula 19 shows a schematic of the tautomerization of an illustrative ligand, in which the tautomerizable unit selected is —C(H,R)— and the metallic central atom M selected, to which the ligand is coordinated, is Ir.

Formula 19

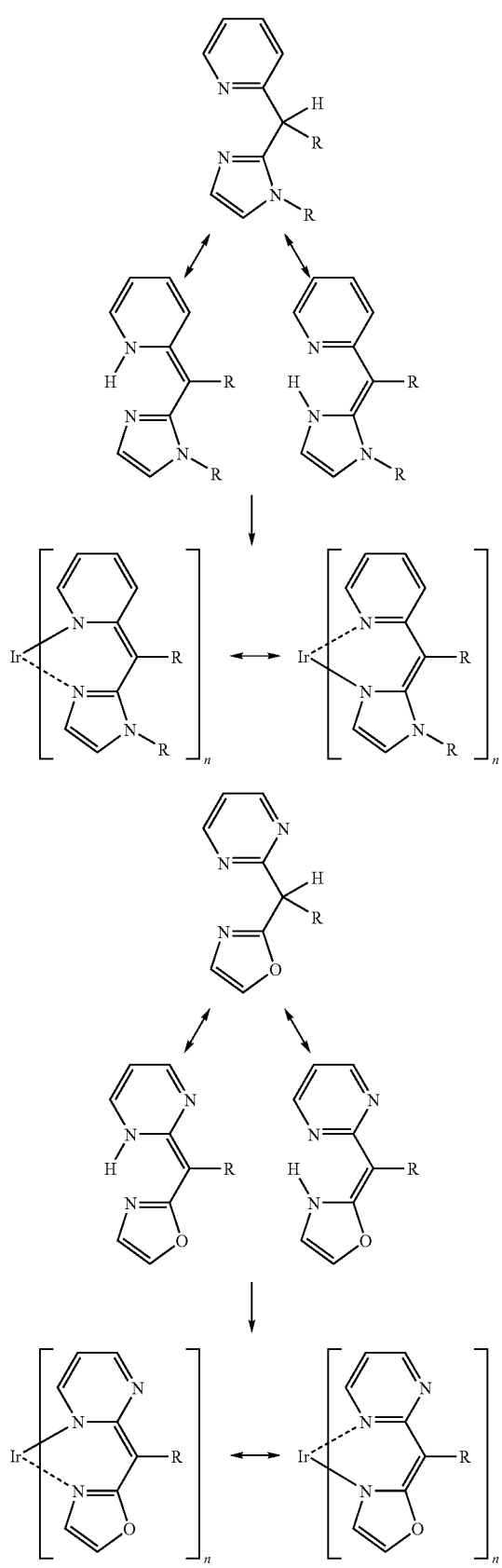

Formula 20

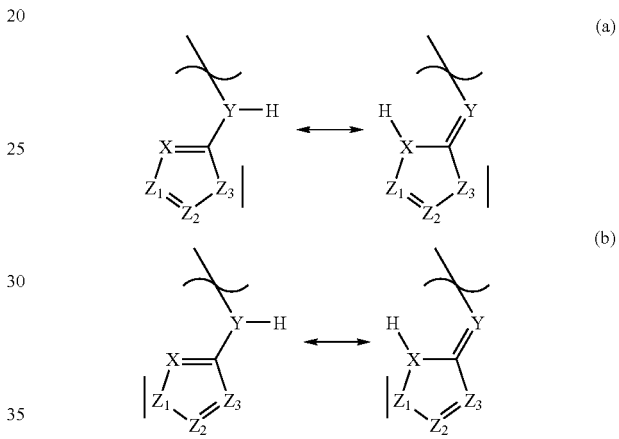

In formula 19, the different possibilities of tautomerization are shown for two different combinations of electron-deficient and electron-rich aromatics in the ligand (formula 19a: combination of pyridine and imidazole, formula 19b: combination of pyrimidine and oxazole). The tautomerized ligand coordinates to the central atom, which here comprises Ir, for example, with elimination of the proton to form the metal complex which is shown in formula 19 in the two mesomeric forms (lower structures in formulae 19a and b).

In addition, $R_4$ and $R_y$, and/or $R_y$, and $R_2$ of the structure shown in formula 17 may also be bridged. The bridges may occur independently of one another.

The tautomerization of five-membered aromatic rings which form part of the ligand is shown schematically in formula 20, where the definitions for the structural formulae of the formula 18 apply analogously to X, Y, $Z_1$, $Z_2$ and $Z_3$.

Electron-deficient five-membered aromatic rings of the formula 20 may be derived, for example, from oxadiazole derivatives when $Z_1$=N, $Z_2$=C—R, $Z_3$=O and X=N. In a five-membered aromatic ring which is derived from thiadiazole derivatives, $Z_1$=N, $Z_2$=C—R, $Z_3$=S and X=N. When the five-membered ring is derived from s-triazole derivatives, $Z_1$=N, $Z_2$=C—R, $Z_3$=N—R and X=N. When the five-membered aromatic ring is derived from tetrazole derivatives, $Z_1$=N, $Z_2$=N, $Z_3$=N—R and X=N.

Electron-rich five-membered aromatics of the formula 20 may be derived, for example, from imidazole derivatives when $Z_1$=C—R, $Z_2$=C—R, $Z_3$=N—R and X=N. When the ring is derived from thiadiazole derivatives, $Z_1$=C—R, $Z_2$=C—R, $Z_3$=S and X=N. In a system derived from oxazole derivatives, $Z_1$=C—R, $Z_2$=C—R, $Z_3$=O and X=N. Derived from selenazole derivatives, $Z_1$=C—R, $Z_2$=C—R, $Z_3$=Se and X=N. When the five-membered ring is derived from oxaphosphole derivatives, $Z_1$=C—R, $Z_2$=C—R, $Z_3$=O and X=P, and, when it is derived from thiaphosphole derivatives, $Z_1$=C—R, $Z_2$=C—R, $Z_3$=S and X=P.

Every R of the electron-deficient and electron-rich aromatic rings may—for each Z differently and independently—be selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. R may be electron-donating and may comprise an amine or an alkoxy group.

Five-membered aromatic rings which are electron-deficient may have a lesser stabilizing effect on the metal complex, and five-membered aromatic rings which are electron-rich may have a stabilizing effect.

Formula 21 shows, by way of example, the tautomerization of a six-membered aromatic ring which may be part of a ligand, where the definitions for the structural formulae of the formula 18 apply analogously to X, Y, $Z_1$, $Z_2$, $Z_3$ and $Z_4$.

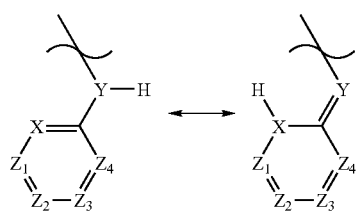

Formula 21

The six-membered ring may, for example, be electron-deficient and may be derived from a pyridine derivative, in which case $Z_1$=C—R, $Z_2$=C—R, $Z_3$=C—R, $Z_4$=C—R and X=N. When the ring is derived from a pyrazine derivative, $Z_1$=C—R, $Z_2$=C—R, $Z_3$=N, $Z_4$=C—R and X=N. In a six-membered ring derived from a pyrimidine derivative, $Z_1$=C—R, $Z_2$=C—R, $Z_3$=C—R, $Z_4$=N and X=N. When the ring is derived from a triazine derivative, $Z_1$=N, $Z_2$=C—R, $Z_3$=C—R, $Z_4$=N and X=N or $Z_1$=C—R, $Z_2$=C—R, $Z_3$=N, $Z_4$=N and X=N.

Each R may—for each Z differently and independently—be selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN. R may be electron-withdrawing and may comprise CN, F, 4-pyridyl, triazyl, 2-pyrimidyl, 5-pyrimidyl, 2-oxazolyl, 4-oxazolyl, 2-thiazolyl, 4-thiazolyl, trifluoromethyl and hexafluoroisopropylidene.

When the six-membered ring of the formula 21 is electron-rich, it may be derived, for example, from a pyridine derivative where $Z_1$=C—R, $Z_2$=C—R, $Z_3$=C—R, $Z_4$=C—R and X=N, where R includes donor substituents which, in addition to those mentioned above, may also be selected from methoxy, dimethylamino and fused five-membered aromatic systems, for example thiophene.

Six-membered aromatic rings which are electron-deficient may have a stabilizing effect on the metal complex.

Additionally provided is a radiation-emitting component which comprises a substrate, at least one lower, first electrode layer on the substrate, at least one organic emitting layer on the first electrode layer, and on top of that at least one upper, second electrode layer, wherein at least one metal complex in which at least one metallic central atom is involved in at least one metallacyclic ring which comprises a tautomerizable unit, where at least one electron-deficient and one electron-rich aromatic are joined via the tautomerizable unit which may comprise H—CR or N—H, are embedded in a matrix in the emitting layer. In addition, the substrate and the first electrode layer may be transparent.

In a further embodiment, the phosphorescent metal complex is polynuclear and has at least two metallic central atoms. At least one central atom thereof forms a six-membered metallacyclic ring with at least one ligand according to the statements made above. Such a compound has a high stability and an adjustability of the emission wavelengths which is dependent on the distance of the central atoms from one another. The emission wavelength may be in the colored, for example light blue, deep blue, blue-green or green range. The distance of the central atoms from one another is adjustable sterically by the selection of the ligands. It is possible to select two or more identical or different central atoms. For example, it is possible for four gold atoms coordinated by ligands to form squares, in which case the corners of the squares are formed by the ligands.

The compound may additionally have at least two metallic central atoms M which are coordinated to one another or bonded to one another via a metal-metal interaction. The two central atoms may additionally be bonded to one another via at least one bridging ligand. There is thus no direct bond between the two central atoms.

A metal-metal interaction is shown schematically in scheme 1.

The bonding scheme shown in scheme 1 shows the bonding conditions between two central atoms according to molecular orbital theory. The molecular orbitals to be occupied are to the left, and the corresponding bond to the right.

Scheme 1

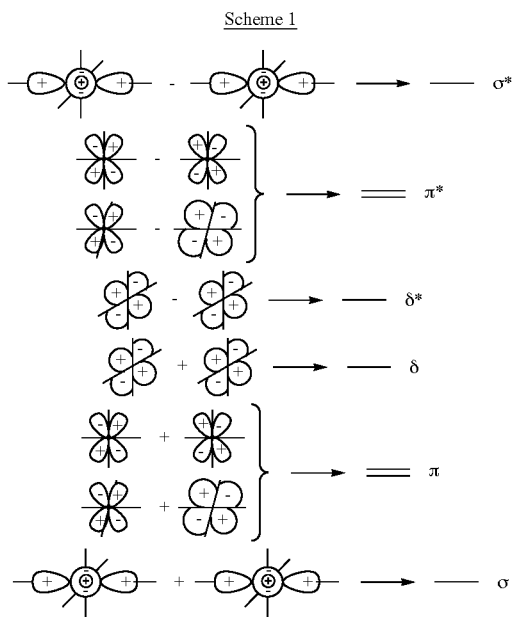

Considering, first of all, the dimeric chromium(II) acetate $Cr_2(OOCH_3)_4$ as an example, 6 electrons arise from each of the two chromium atoms, and 2×2 electrons from each of the four acetate ligands, i.e. a total of 28 electrons. In order that the chromium atoms can each fulfill the 18-electron rule, i.e. achieve a configuration with 18 outer electrons in each case (36 electrons in total), they form a quadruple bond with one another. There is thus a $\sigma^2\pi^4\delta^2$ configuration.

In comparison, an example of a binuclear metal complex is considered. An illustrative compound considered is phenylpyridine-Pt-(μ-pyrazole)$_2$-Pt-phenylpyridine. Here, there are 2×10 electrons from the two platinum atoms, 2×4 electrons from the pyrazole ligands and 2×4 electrons from the phenylpyridine ligands, i.e. 36 electrons in total. The 18-electron rule is thus already fulfilled for the two platinum atoms, and there is a $\sigma^2\pi^4\delta^{*2}\pi^{*4}\sigma^{*2}$ configuration and hence, in a formal sense, no bond between the two platinum atoms is present since the bonding and non-bonding orbitals cancel each other out. The two platinum atoms, however, show a distance of 3 ångström, which is caused by a significant interaction between the two platinum atoms.

Considered in a formal sense, it is thus also possible to decouple hole and electron transport from one another. The hole transport can take place in the non-bonding $\sigma^*$ orbital, whereas the electron transport takes place in the $\pi^*$ orbital of the ligand. The hole transport, which corresponds to an oxidation, formally generates a bond order of 0.5, which stabilizes the compound. Electron transport, which corresponds to a reduction, can be stabilized by the six-membered metallacyclic ring.

Ligands which can form a six-membered ring with the metallic central atom, as described in the above and further remarks, are bidentate ligands which coordinate to the central atom with two bonding atoms. These two bonding atoms are in 1,5 positions relative to one another.

Bridging ligands which bridge two central atoms to one another, as described in the further remarks, are likewise bidentate ligands which coordinate by one bonding atom each to one central atom each. The bonding atoms of the bridging ligands have a 1,2 or 1,3 arrangement relative to one another.

The at least one bridging ligand may be selected from a group which comprises guanidine derivatives and pyrazole derivatives. The bridging ligands may be selected, for example, from 1,3,4,6,7,8-hexahydro-2H-pyrimido[1,2-a]pyrimidine (hpp) and pyrazole. However, further conceivable bridging ligands are also those which have bonding atoms which have a 1, 2 or 1,3 arrangement relative to one another and are selected from O, N and S. Illustrative bridging ligands are specified in "Multiple Bonds between Atoms", Cotton, Murillo, Walton, Springerverlag and in Inorg. Chem., Vol. 41, No. 12, 2002, page 3055. Formula 22 shows an hpp bridging ligand in which the electron delocalized between the three nitrogen atoms is also indicated. Hpp bridging ligands which coordinate to two central atoms always have a delocalized electron as in formula 22. In the formulae which include hpp bridging ligands shown hereinafter, this applies analogously, even though, for the sake of clarity, the hpp ligand is shown with a double bond or without a double bond and the delocalized electron is not indicated.

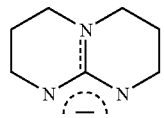

Formula 22

When a polynuclear metal complex has bridging ligands, this can enhance the phosphorescence of the compound. For example, a compound with hpp as a bridging ligand exhibits increased phosphorescence compared to metal complexes which have no bridging ligands or which have no six-membered metallacyclic rings with ligands.

The bridging ligands may also be formed from the $R_1$ and/or $R_5$ radicals of the structures of the formulae 3, 5, 12, 13 and 17 of the ligands.

In a further embodiment, the polynuclear phosphorescent metal complex has at least two metallic central atoms to which the ligands are coordinated, which form a five-membered metallacyclic ring with a central atom, the central atoms being joined to one another by bridging ligands. The bridging ligands may, for example, comprise guanidine derivatives or pyrazole derivatives. These compounds may emit light of a color which is selected, for example, from deep blue, light blue, blue-green and green. In addition, these compounds have a high stability.

Additionally provided is a radiation-emitting component which comprises a substrate, a first electrode layer on the substrate, at least one organic emitting layer on the first electrode layer and a second electrode layer on the organic emitting layer. The organic emitting layer comprises a phosphorescent metal complex according to the above remarks.

"On" as already used above means that the layers are arranged one on top of another. However, it is also possible for further layers to be present between the layers mentioned.

Examples of further layers which may be present in the component include electron or hole transport layers, electron or hole blocking layers, electron or hole injection layers, or else a plurality of organic emitting layers.

The metal complex may be present in a matrix material. This allows the concentration of emitting material in the matrix material and the intensity of the emitted radiation to be adjusted.

On application of a voltage, the component may emit light of a color which is selected from a group which comprises deep blue, light blue, blue-green and green. This provides a radiation-emitting component which emits blue light, for example. In further embodiments, the component may also emit light of further colors. When the component comprises further emitting layers which emit light of other colors, it is possible to provide a white light-emitting component in combination with the deep blue-, light blue-, blue-green- or green-emitting layer.

The component may have a transparent substrate and a transparent first electrode layer or a transparent second electrode layer or a transparent substrate, a transparent first electrode layer and a transparent second electrode layer. It is accordingly a bottom-emitting component, a top-emitting component or a component which emits on both sides.

The radiation-emitting component may, for example, be an organic light-emitting diode (OLED).

In a further embodiment, the component may comprise at least two electrodes with an organic semiconductor material in between, wherein the semiconductor material comprises blue-phosphorescing organic transition metal complexes of heavy elements of transition group 8 of the A and B types,

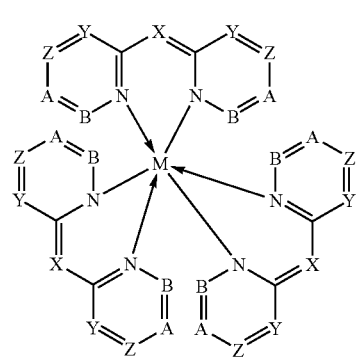

A

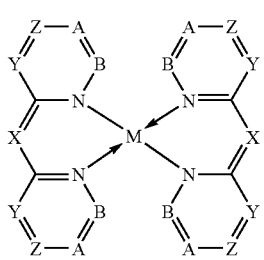

where:
metal M in the octahedral complexes A is iridium, rhodium or rhenium; in the square complexes B, platinum is the central atom;
the rest of the variables may each independently be nitrogen or carbon, where the free valence in the case of carbon is satisfied by hydrogen or another substituent.

Possible substituents include alkyl, cyano or aromatic and/or heteroaromatic moieties, but particularly those which form a fused aromatic and/or heteroaromatic cyclic substituent between two variables in each case.

Since the ligand structures can also be considered as symmetric polymethines, the octahedral complexes cannot be distinguished into meridional and facial complexes. The square platinum complexes also have polymethine-like ligands.

The lower the π-electron density of the aromatics, the shorter-wave is the absorption and emission wavelength of the complex.

These novel phosphorescent semiconductor materials can thus, for example, cover the entire blue-emitting spectral range. The semiconductor materials have a high chemical stability, thermal stability and photo-stability.

Particular stability arises in the complexes through the symmetry of the two ligand-metal bonds, which are mesomeric and therefore indistinguishable.

The semiconductor materials can be prepared by the following reaction scheme:

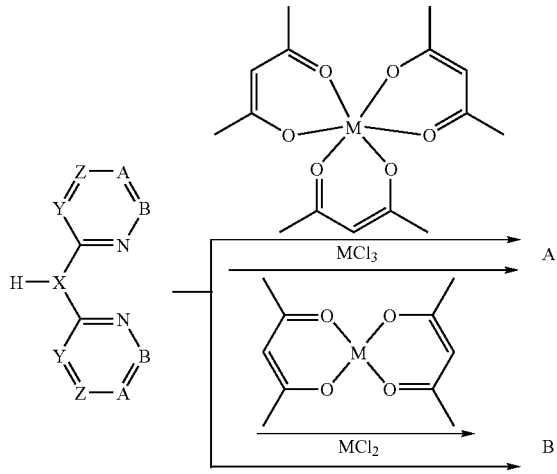

The polymethine-like azaaromatic is heated with the particular metal salts (preferably chlorides) or with the acetylacetonate complexes of the particular metals in boiling polar solvents, preferably in the presence of an auxiliary base such as sodium carbonate, in stoichiometric ratios and an inert gas atmosphere at reflux for 10-20 h.

Extraction of the water-diluted reaction mixtures by means of methylene chloride or chloroform provides the raw materials, which are purified by sublimation.

Also provided is a process for preparing a phosphorescent metal complex according to the above statements. The process comprises the process steps of A) providing a central atom compound of a metallic central atom, having exchange ligands coordinated to the central atom, B) mixing the central atom compound and a ligand dissolved in a first solvent in a stoichiometric ratio to form the metal complex, wherein the exchange ligand is replaced by the ligand and the ligand has a tautomerizable unit and forms a six-membered metallacyclic ring with the central atom with elimination of a proton. In the process, the proton can be eliminated by adding auxiliary bases which are selected from a group comprising triethylamine, pyridine and alkali metal carbonate.

In addition, in process step A), the central atom compound of a metallic central atom can be dissolved in degassed hot water, cooled and crystallized as a fine suspension. The cooling can be effected with vigorous stirring. The hot water may have a temperature of 80° C. to 100° C. and the solution composed of water and central atom compound can be cooled to a temperature of 20° C. to 30° C. In the course of cooling, the fine suspension precipitates. This process step can convert a coarse particulate central atom compound to a fine particulate central atom compound, and additionally remove oxygen residues from the central atom compound. The central atom compound may, for example, be a salt, and the exchange ligands may be halogen ions.

The salt of the metallic central atom may, for example, be potassium tetrachloroplatinate $K_2PtCl_4$. However, conceivable salts are also those with Ir, Au, Pt, Re, Rh, Ru, Os, Pd, Ag, Zn, Al, lanthanoids and further metals and transition metals with an atomic number of >35, further halogen ions and further cations such as $Na^+$, $K^+$ or $NH_4^+$.

In addition, in process step B), a first solvent which is miscible with polar and nonpolar solvents can be selected. This may, for example, be ethoxyethanol. The ligand is dissolved in the first solvent and is tautomerizable. When the ligand coordinates to the central atom, this eliminates a proton from the ligand. A metal complex is formed, in which the ligand has mesomerism, as shown, for example, in formula 19.

In addition, in process step B), a mononuclear metal complex may be formed. The mixture of dissolved ligand and the central atom compound can be heated, which forms the metal complex. This metal complex has at least one ligand which forms a six-membered metallacyclic complex with the central atom, as shown, for example, in formula 3.

When a mononuclear metal complex is formed, the stoichiometric ratio $$\frac{\text{amount (ligand)}}{\text{amount (central atom compound)}}$$

may correspond to the ratio $$\frac{\text{number of ligands coordinated to the central atom}}{1}.$$

Thus, as many ligands as will be coordinated to the central atom of the mononuclear compound are used, in order that the central atom is saturated. For instance, the ratio $$\frac{\text{amount (ligand)}}{\text{amount (central atom compound)}}$$

may, for example, be 2:1.

In a further embodiment, process step B) comprises the process steps of

B1) mixing the central atom compound and a ligand dissolved in a first solvent in a stoichiometric ratio to form a polynuclear transition complex, B2) dissolving the transition complex in a second solvent and mixing the dissolved transition complex with an additional ligand dissolved in a third solvent in a stoichiometric ratio, B3) forming the metal complex with dissolution of the transition complex. The first, second and third solvents may be the same or different.

The transition complex formed in process step B1) may have at least two metallic central atoms, to each of which is coordinated at least one ligand in a six-membered metallacyclic ring, and which are bridged to one another via at least one exchange ligand of the central atom compound. Such a transition complex may, for example, have a structure of the formula 23.

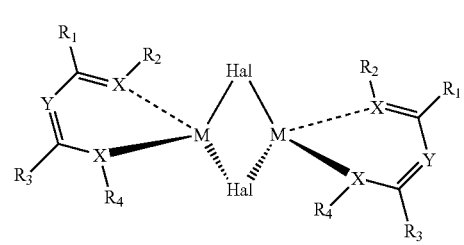

Formula 23

In formula 23, Hal denotes the exchange ligand, for example a halogen ion, which may be Cl, for example, which serves as a bridging ligand between two central atoms M. Hal may, however, also be any further readily exchangeable ligand, for example trifluoromethane-sulfonate, CO or acetylacetonate. The definitions of M, X, Y and $R_1$ to $R_4$ are each analogous to the definitions cited for formula 3.

The stoichiometric ratio $$\frac{\text{amount (ligand)}}{\text{amount (central atom compound)}}$$

in process step B1) may correspond to the ratio $$\frac{\text{number of ligands coordinated to a central atom in the transition complex}}{1}$$

This ratio may, for example, be 1:1. The number of ligands used thus corresponds to the number of ligands coordinated to a central atom, in order that the central atom is saturated when at least one exchange ligand is additionally also coordinated to the central atom. In formula 23, for example, two central atoms M are bridged via two halogen ions Hal and each also have a ligand with which they form a six-membered metallacyclic ring.

Furthermore, in process step B2), the second and third solvents selected may be basic solvents or solvents to which a base is added. The base added may, for example, be $NaOR^-$, $KOR^-$, NaH or carbonates, where R comprises an organic radical. For example, the second solvent may comprise dichloromethane and the third solvent dichloromethane in which sodium methoxide is dissolved or with which sodium ethoxide forms a suspension.

Further useful second and/or third solvents are sodium bicarbonate and triethylamine, and also alkoxides and halohydrocarbons. The basic third solvent in which the additional ligand is dissolved can bring about deprotonation of the additional ligand, and hence enable coordination of the additional ligand to the central atom. The dissolved transition complex and the dissolved additional ligand can be cooled and mixed, and this mixture can be stirred at room temperature. The solutions can be cooled, for example, to a temperature of −70° C., and the mixture can be stirred, for example, for 48 h.

In addition, in process step B2), a stoichiometric ratio $$\frac{\text{amount (additional ligand)}}{\text{amount (transition complex)}}$$

may correspond to the ratio $$\frac{\text{number of central atoms present in the transition complex}}{1}.$$

With this amount of additional ligand, the exchange ligands which bridge the central atoms, for example halogen ions, can be exchanged for additional ligands.

Furthermore, in process step B2), it is possible to select an additional ligand which forms a five-membered or six-membered metallacyclic ring with the central atom. It is thus possible to prepare a mononuclear compound. It is possible, for example, to select a ligand which is already used in process step B1). Further ligands which can form six-membered metallacyclic rings with the central atom, for example with a structure of the formula 3, can likewise be used. Examples of ligands which form five-membered metallacyclic rings with the central atom are phenylpyridine derivatives, arylimidazole derivatives or arylcarbene derivatives.

When such a ligand is selected as an additional ligand in process step B2), it is possible in process step B3) to form a mononuclear metal complex which has at least one ligand with which the central atom forms a six-membered metallacyclic ring. Such a mononuclear metal complex may have, for example, a structure of the formula 3.

In addition, in process step B2), the additional ligand selected may be a bridging ligand. It is thus possible to prepare a polynuclear compound in which central atoms are joined to one another by bridging ligands. A bridging ligand is, for example, selected from guanidine derivatives or pyrazole derivatives. Guanidine derivatives can be prepared, for example, by a preparation process as disclosed in Dalton Trans., 2006, 4623-4631. Reference is hereby made completely to this preparation process. A bridging ligand is, for example, a bidentate ligand with two bonding atoms which are in a 1,2 or 1,3 arrangement relative to one another. The formation of a six- or five-membered ring with a central atom is therefore impossible. The formation of, for example, dimeric metal complexes is thus promoted.

It is possible in process step B3)—when a bridging ligand is selected as the additional ligand in process step B2)—to form a polynuclear metal complex which comprises at least one ligand with which a central atom forms a six-membered metallacyclic ring, and in which at least two central atoms in each case are bridged to one another via at least one bridging ligand. Given appropriate adjustment of the stoichiometric ratio, it is additionally also possible to form clusters with more than two central atoms.

Process steps A), B), B1), B2) and B3) can be performed in an inert atmosphere, for example in an argon or nitrogen atmosphere.

the counter ion K may likewise vary. In a first synthesis step, the salt I is reacted with a ligand II. The latter has a tautomerizable structural unit Y which may, for example, be $CH_2$ or N—H. Elimination of a proton in process step B1) forms a transition complex III which here comprises two central atoms M with one ligand each, the two central atoms being joined to one another via two halogen ions.

When the transition complex III is reacted in process step B2) with a ligand with which a central atom can form five- or six-membered metallacyclic rings, a mononuclear metal complex VI forms in process step B3). In scheme 2, the ligand II is selected as such a ligand, but it is also possible to select a ligand other than ligand II. According to the valency of the central atom, 1 to 3 ligands may be coordinated to the central

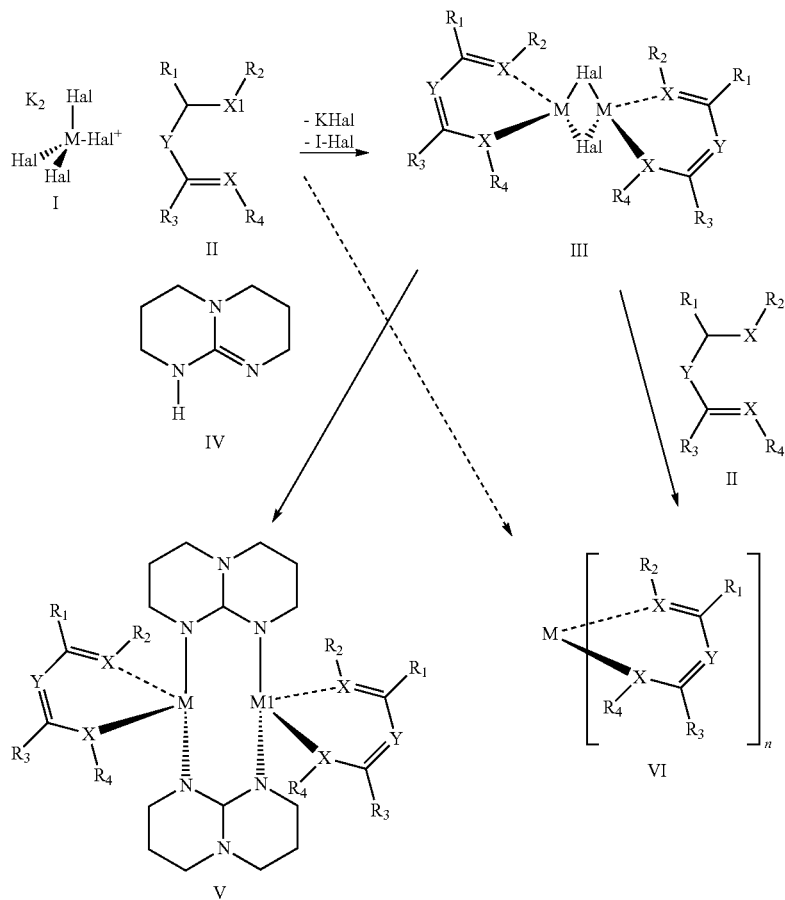

Scheme 2 shows one synthesis route for mono- and polynuclear metal complexes by the process described above. The stoichiometric ratios are not specified in scheme 2, since they may be different according to the desired product, as was detailed above.

A central atom compound specified by way of example in scheme 2 is a salt of a metallic central atom which has halogen ions Hal as exchange ligands. Instead of halogen ions, it is additionally possible to use readily exchangeable ligands, for example acetyl-acetonate, trifluoromethanesulfonate or CO. The salt I of a metallic central atom M has here, by way of example, four halogen ions Hal; the number of halogen ions coordinated to the central atom M may, however, vary according to the valency of the central atom M. The ratio relative to atom, i.e. n may be 1 to 3. In scheme 2, a central atom M to which two ligands coordinate is selected by way of example, as can be seen in structure III and V.

The mononuclear metal complex VI may additionally be formed directly from the salt I and the ligand II in process step B) when the stoichiometric ratio between salt and ligand is adjusted appropriately (dotted arrow).

When the transition complex III is reacted with a bridging ligand IV in process step B2), a polynuclear metal complex V forms in process step B3). In scheme 2, the bridging ligand selected by way of example is an hpp ligand; any other bridging ligand can be used analogously. The polynuclear metal complex in this example has two central atoms M with one ligand each, which are joined to one another via two bridging ligands.

In a further embodiment of the process, it is possible in process step B1) to select a ligand which forms a five-membered metallacyclic ring with the central atom. In this case, a transition complex which comprises central atoms to each of which is coordinated at least one ligand which forms a five-membered metallacyclic ring with the central atom is prepared. This transition complex can be reacted in process step B2) with an additional ligand which is a bridging ligand. Thus, in process step B3), a polynuclear compound is obtained, which has at least one bridging ligand and forms five-membered metallacyclic rings with the ligands.

DETAILED DESCRIPTION OF THE DRAWINGS

Examples of compounds which have a carbene ligand are shown in formula 24. For all compounds shown there, for example, M may be Ir when n=3. When n=2 and M=Ir, an additional ligand, for example a picolinate anion, phenylpyridine and 2-phenylimidazole, is then also present. Analogously, when n=1 and M=Ir, two additional ligands are also present.

Formula 24

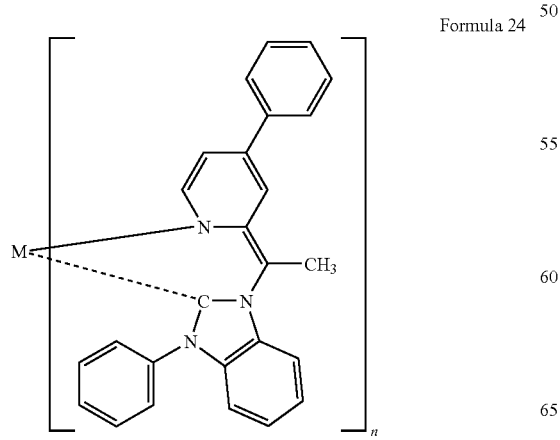

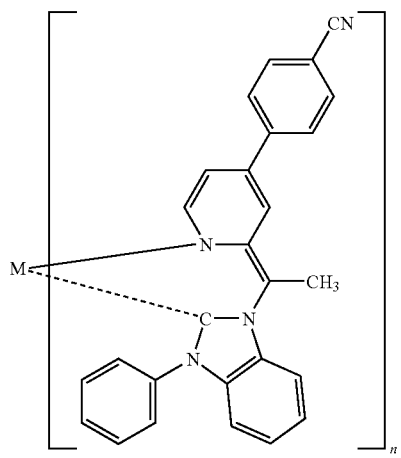

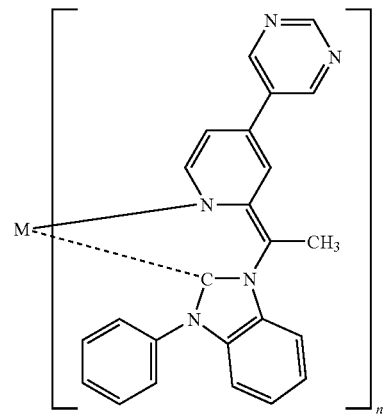

Formula 25
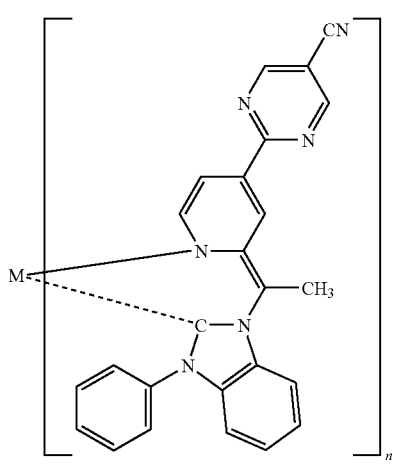
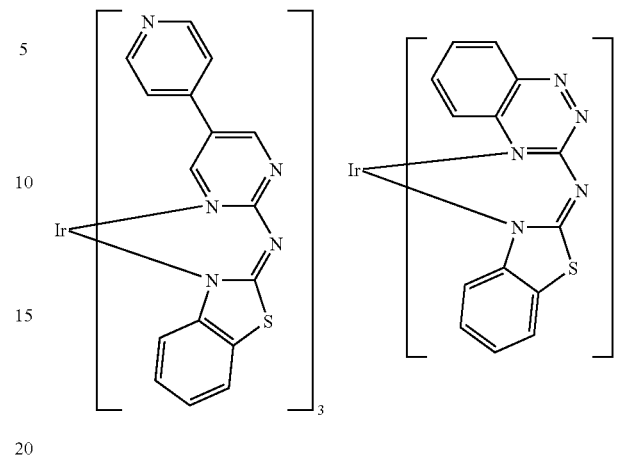
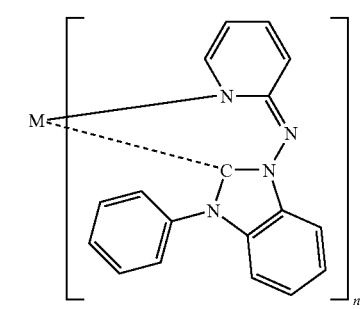
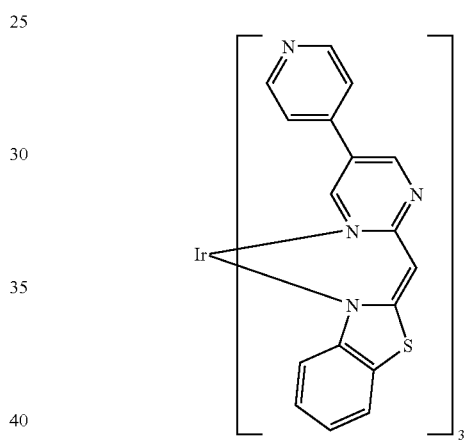
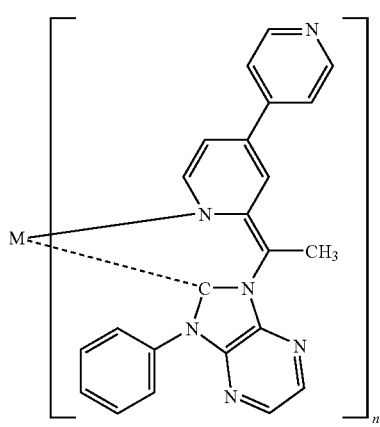
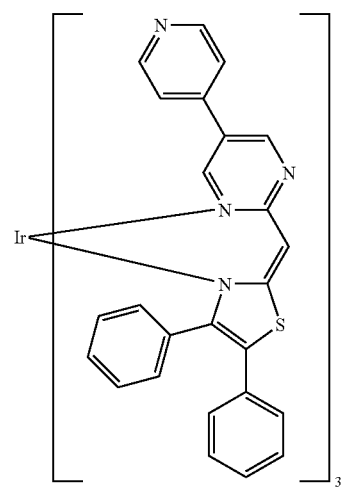
Examples of compounds which have a ligand with one electron-deficient and one electron-rich aromatic ring are shown in formula 25. The central atom here is Ir; further central atoms are equally suitable.

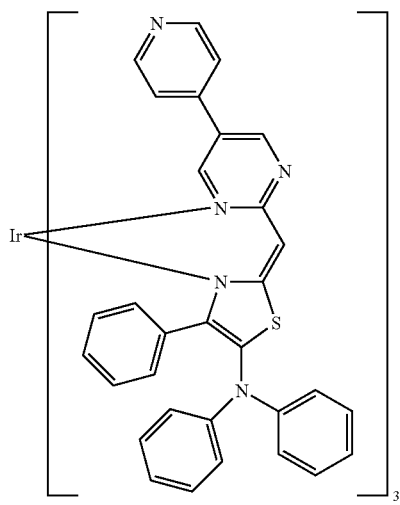

Examples of compounds which are binuclear are given hereinafter.

Formula 26 shows examples of a binuclear compound with Pt as central atoms and 1,3,4,6,7,8-hexahydro-2H-pyrimido[1,2-a]pyrimidine (a) and pyrazole (b) as bridging ligands, where, for R, substituents according to the statements made above are selected from H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

Formula 26

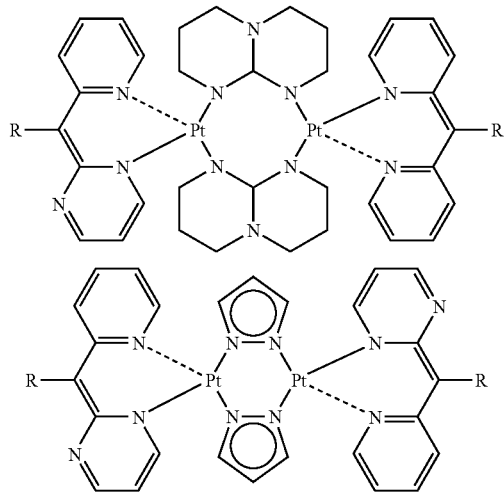

Formula 27 shows examples of compounds with Ir as central atoms, 1,3,4,6,7,8-hexahydro-2H-pyrimido[1,2-a]pyrimidine (a) and pyrazole (b) as bridging ligands, where either two bridging ligands and two ligands on each Ir, or four bridging ligands and one ligand on each Ir, may be present. R may be selected analogously to formula 26.

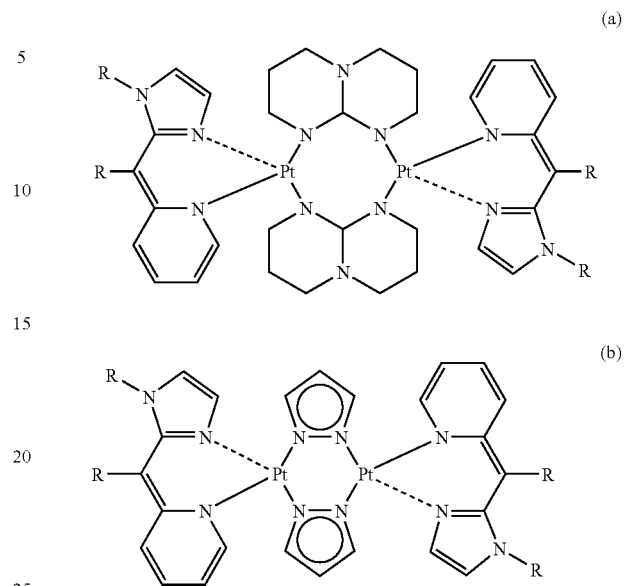

Formula 27

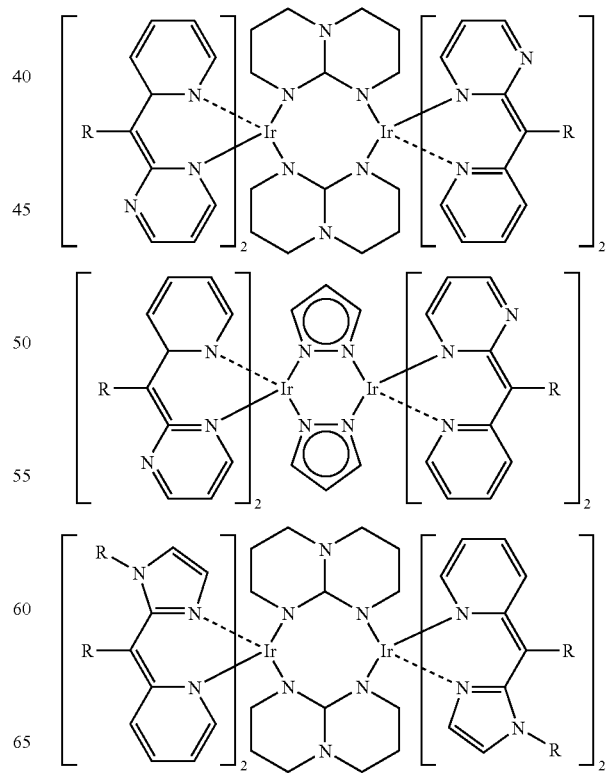

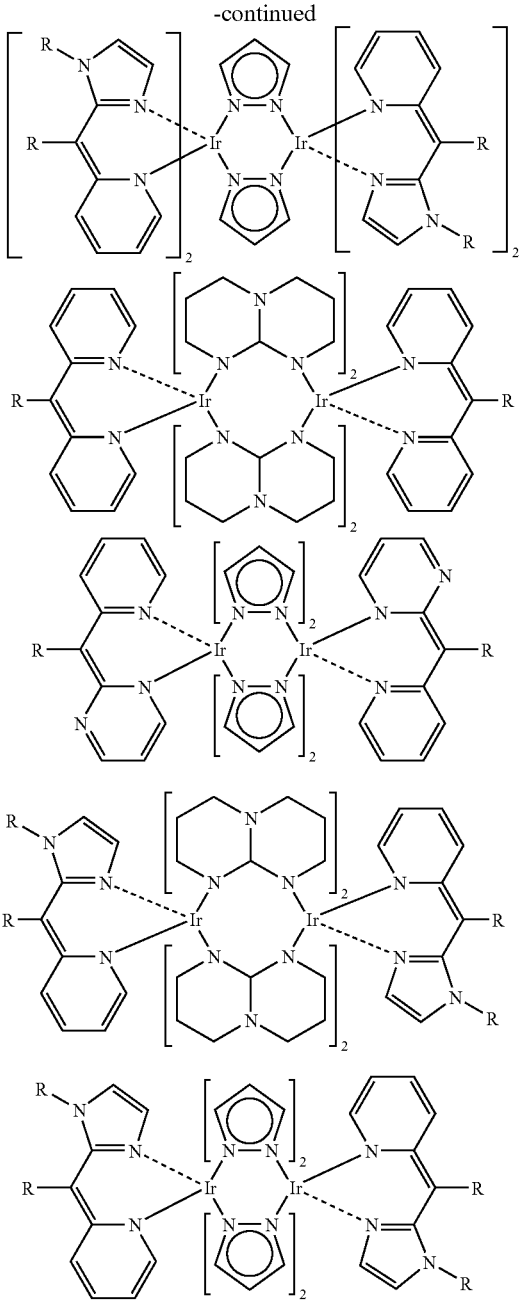

(a)

(b)

The structural formulae shown in the formulae 26a and 27a may also have N—C—N units as bridging ligands, which are integrated into a five-membered, six-membered or seven-membered ring, or which are substituted without ring formation.

Figure 1:
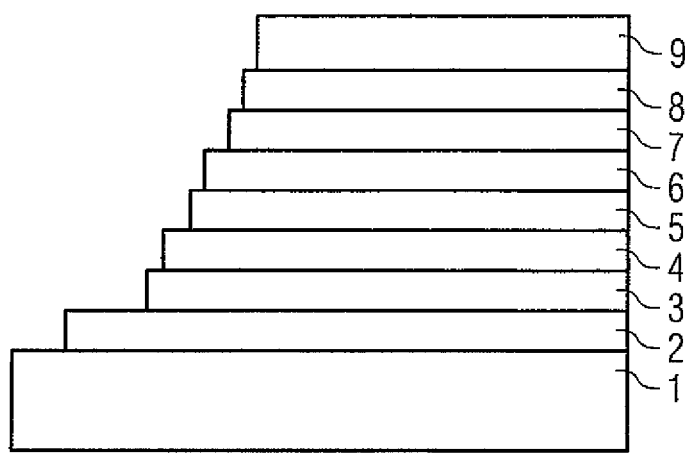
FIG. 1 shows the schematic side view of a radiation-emitting component.

FIG. 1 shows the schematic side view of a radiation-emitting component. On a substrate 1, which is made of glass, for example, is arranged a first electrode layer 2 which is, for example, transparent and made of ITO (indium tin oxide). On this electrode layer 2 is arranged a hole injection layer 3, on which in turn is arranged a hole transport layer 4. On the hole transport layer 4 is arranged an organic active layer, the organic emitting layer 5, on which are arranged a hole blocking layer 6, an electron transport layer 7 and an electron injection layer 8. On the electron injection layer 8 is arranged a second electrode layer 9, for example a metal electrode.

On application of a voltage between first and second electrode layers 2, 9, current flows through the component and photons are released in the emission layer 5 and leave the component in the form of light, for example through the first electrode layer 2 and the substrate 1. Alternatively, it is also possible for the second electrode layer 9 to additionally or solely have a transparent configuration, and for the light to leave the component through both electrode layers or only through the second electrode layer.

The emission layer 5 comprises metal complexes according to the above statements, which may be embedded in a matrix.

Figure 2:
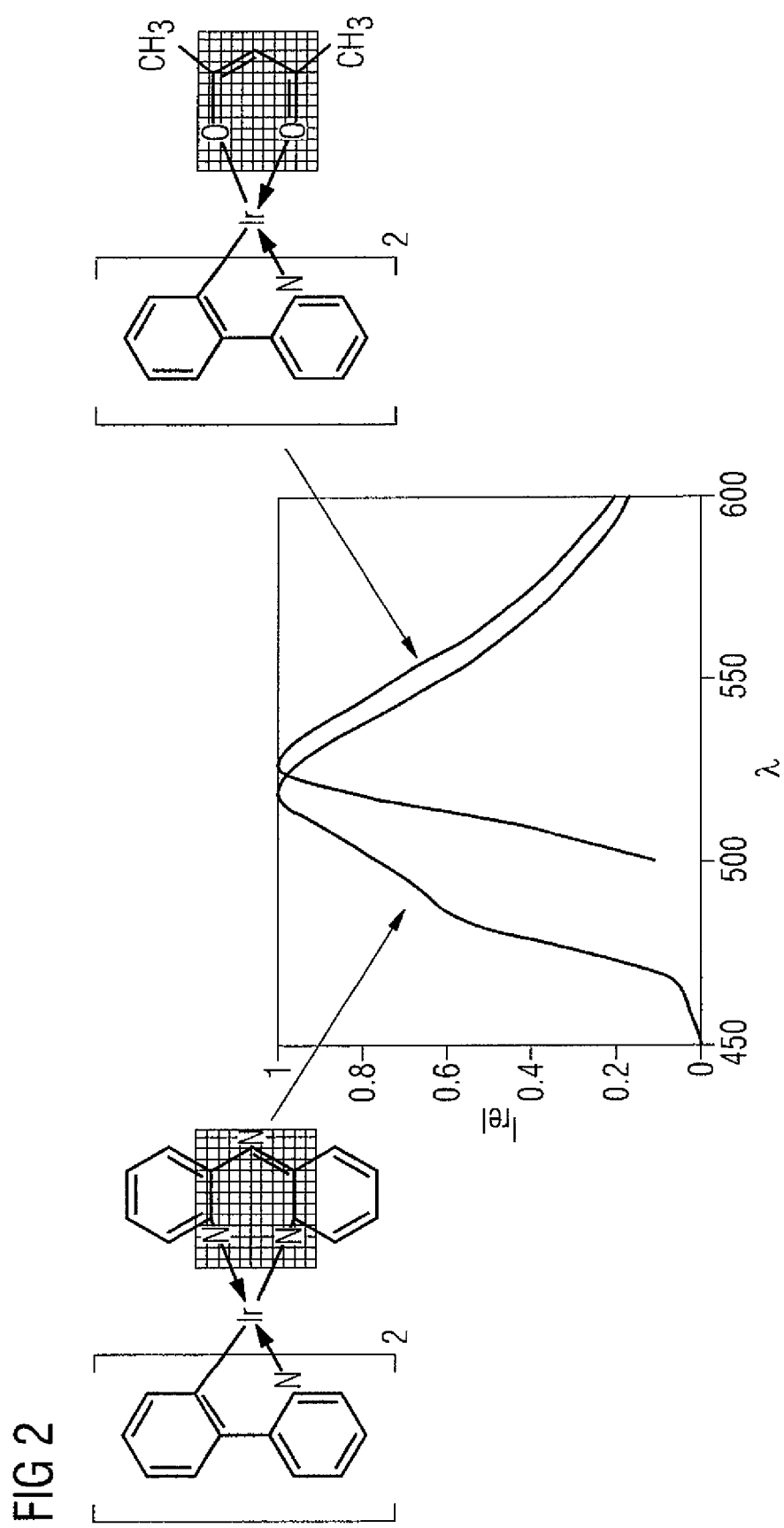
FIG. 2 shows a photoluminescence spectrum of a metal complex compared to a conventional metal complex.

FIG. 2 shows a comparison of photoluminescence spectra of two metal complexes with a six-membered metallacyclic ring, which differ by the affinity of the ligand for the central atom, ((phenylpyridyl)$_2$Ir(di-pyridylamine) and (phenylpyridyl)$_2$Ir(acetylacetonate)). The wavelength $\lambda$ in nm is plotted against the relative intensity $I_{rel}$. It is evident that, as a result of the introduction of the more nucleophilic aza-analogous 1,3-diketone ligand 2,2-dipyridylamine, a shift of the light emitted to shorter wavelengths by about 10 nm takes place. The breadth of the spectra is obtained as a result of the heterolepticity of the complexes; the five-membered metallacycles emit above 500 nm; the increasing influence of the component (2,2-dipyridyl-amine) which forms the more affinitive six-membered metallacycles intensifies the emission of blue light (wavelengths less than 500 nm).

(Phenylpyridyl)$_2$Ir(dipyridylamine) can be prepared from (phenylpyridyl)$_2$Ir(acetylacetonate), for example, by heating (phenylpyridyl)$_2$Ir(acetylacetonate) with the equivalent amount of dipyridylamine in ethoxyethanol for 1 to 2 min until the orange color changes to yellow. After cooling, the product is filtered off with suction and washed with methanol. This reaction takes place with a yield of 95%. The reaction shows that the formation of a six-membered metallacyclic ring with a tautomerizable unit of the ligand, which forms an aza-analogous 1,3-diketonate complex with the central atom, is energetically favored owing to the increased nucleophilicity.

Alternatively, (Phenylpyridyl)$_2$Ir(dipyridylamine) can be prepared by boiling 0.1 mmol (107 mg) of (phenyl-pyridine) di-μ-chloroiridium(III) complex, 0.2 mmol (35 mg) of dipyridylamine and 0.2 mmol (168 mg) of sodium bicarbonate in 20 ml of ethoxyethanol at reflux in a 100 ml flask for 30 min. In the course of this, yellow product precipitates out, which is filtered off with suction and washed with methanol (75% yield).

Working examples for preparation of transition complexes and metal complexes are given hereinafter.

Synthesis of di(μ-chloro)bis[(phenylpyridino)-platinum(II)]=Compound 1

Compound 1

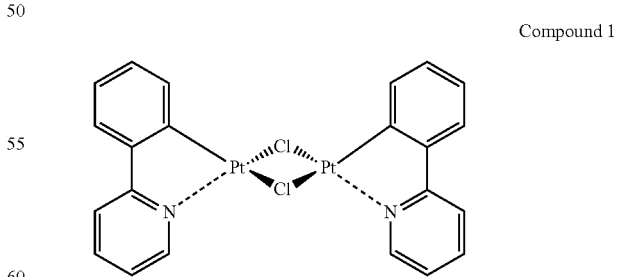

12 mmol (4.98 g) of potassium tetrachloroplatinate are dissolved in 24 ml of hot degassed water and cooled again with vigorous stirring. In the course of this, the potassium tetrachloroplatinate precipitates out as a fine suspension. A solution of 12 mmol (1.86 g) of phenylpyridine in 72 ml of ethoxyethanol is added dropwise to this suspension. The suspension is heated to 70° C., which increasingly forms a dark green precipitate. To precipitate the crude product, the suspension is blanketed with 30 ml of water and stirred after approx. 2 h. The crude product is filtered off with suction and washed repeatedly with a water/alcohol mixture (10:1). At this point, the product becomes air-stable. Subsequently, it is dried under reduced pressure for approx. 20 h. Different batches exhibit a yellow to green color in the solid according to the proportion of impurities. However, the crude product can be used for the further experiments without further purification.

Yield: 3.56 g (77.2%)

Synthesis of di(μ-chloro)bis[(2,4-difluorophenyl-pyridino)platinum(II)]=Compound 2

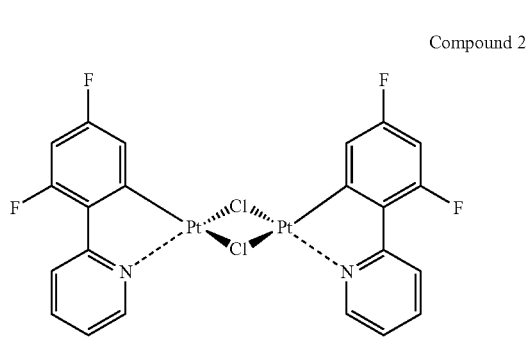

Compound 2

7.23 mmol (3 g) of potassium tetrachloroplatinate are dissolved in 14 ml of hot degassed water and cooled to 30° C. with vigorous stirring. In the course of this, the potassium tetrachloroplatinate precipitates out as a fine suspension. A solution of 7.23 mmol (1.387 g) of 2,4-difluorophenylpyridine in 42 ml of ethoxyethanol is slowly added dropwise to this suspension. The suspension is heated to 70° C. for approx. 20 h, in the course of which a yellow-green precipitate increasingly forms. After cooling to room temperature, the crude product is precipitated by blanketing the suspension with 30 ml of water and stirring it after approx. 2 h. The yellow-green crude product is filtered off with suction and washed repeatedly with a water/alcohol mixture (10:1). Dry in a desiccator under reduced pressure for approx. 20 h.

Yield: 2.36 g (78%)

Compounds 1 and 2 show the synthesis of a transition complex with selection of ligands which form five-membered metallacyclic rings with the central atom.

Synthesis of di(g-chloro)bis[(dipyridylamino)-platinum(II)]=Compound 3

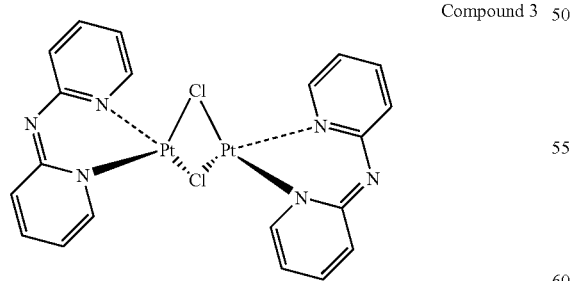

Compound 3

3 mmol (1.245 g) of potassium tetrachloroplatinate are dissolved in 6 ml of hot degassed water and cooled to 30° C. with vigorous stirring. In the course of this, the potassium tetrachloroplatinate precipitates out as a fine suspension. A solution of 3 mmol (0.514 g) of dipyridylamine in 45 ml of ethoxyethanol is slowly added dropwise to this suspension. The suspension is heated to 70° C. for approx. 20 h, in the course of which a cream-colored precipitate increasingly forms. After cooling to room temperature, the crude product is precipitated by blanketing the suspension with 40 ml of water and stirring it after approx. 2 h. The crude product is filtered off with suction and washed repeatedly with a water/alcohol mixture (10:1). Dry in a desiccator under reduced pressure for approx. 20 h.

Yield: 1 g (83%).

Compound 3 shows an example of a metal complex which forms a six-membered metallacyclic ring with the ligand.

Synthesis of bis[(dipyridylamino)platinum(II)]=Compound 4

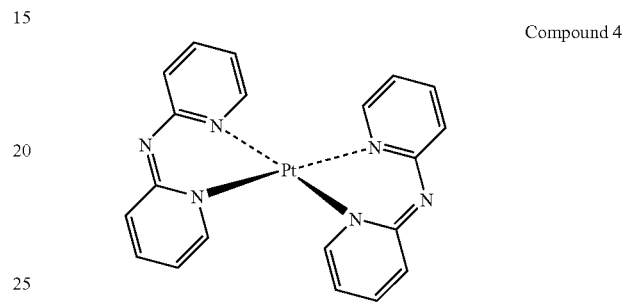

Compound 4

3 mmol (1.245 g) of potassium tetrachloroplatinate are dissolved in 6 ml of hot degassed water and cooled to 30° C. with vigorous stirring. In the course of this, the potassium tetrachloroplatinate precipitates out as a fine suspension. A solution of 6 mmol (1.027 g) of dipyridylamine in 40 ml of ethoxyethanol is slowly added dropwise to this suspension. The suspension is heated to 70° C. for approx. 20 h, in the course of which a yellow precipitate increasingly forms. After cooling, the mixture is admixed twice with 50 ml each time of water and heated with stirring in order to extract the product. The water phase is removed and concentrated by rotary evaporation, and the yellow product is taken up in methanol and filtered in order to remove the potassium chloride formed. Then draw off the methanol under reduced pressure.

Yield: 1.37 g (85%)

This compound can be detected by means of mass spectrometry.

Figure 3A:
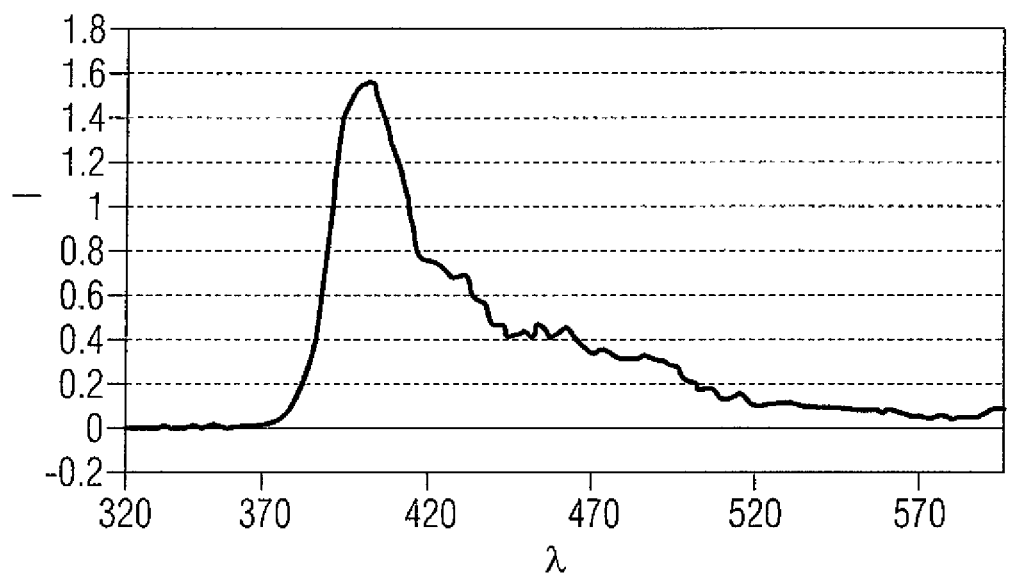
FIGS. 3a to j show photoluminescence spectra for various metal complexes.
Figure 3B:
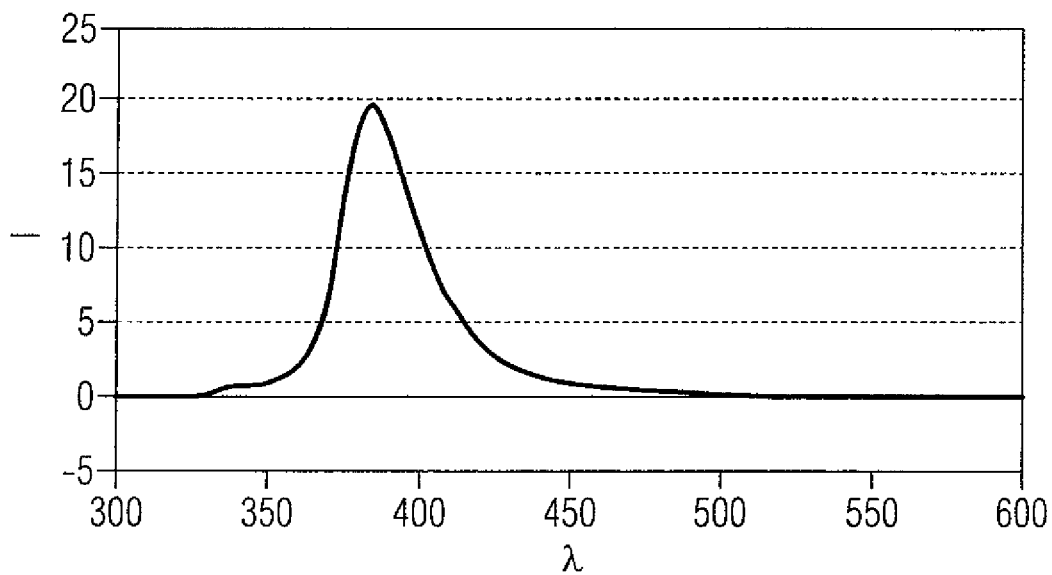
Figure 3C:
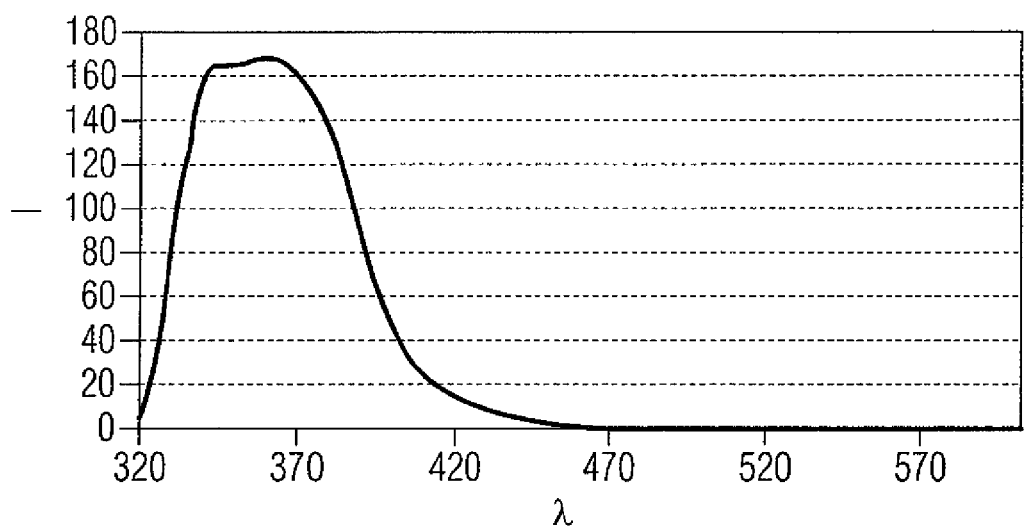
Figure 3D:
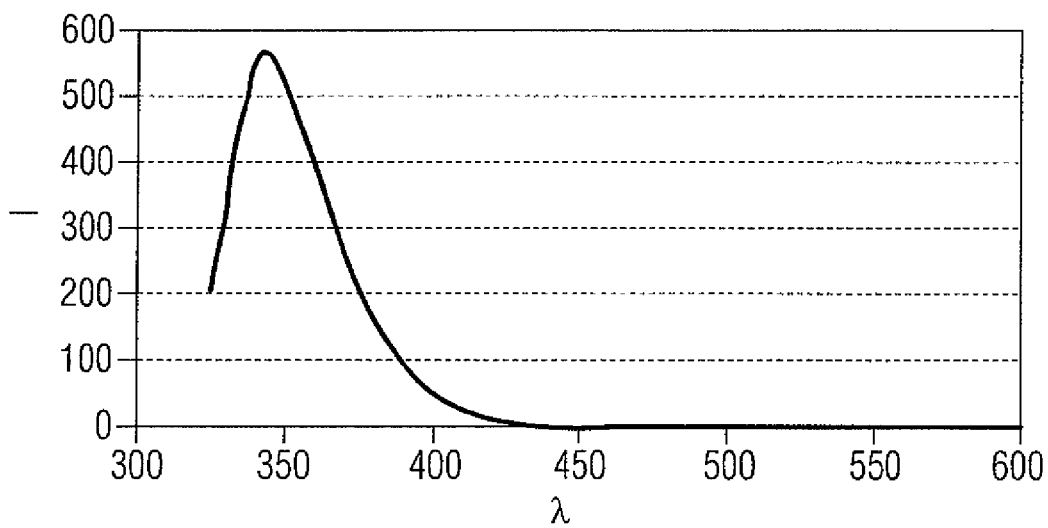

Compound 4 shows a mononuclear metal complex in which the central atom forms six-membered metallacyclic rings with the ligands. FIGS. 3a, b, c and d show photoluminescence spectra of this compound in different dilutions. With increasing dilution, the emission maximum shifts from approx. 398 nm to 345 nm.

Synthesis of bis[(difluorophenylpyridino)platinum(II)]=Compound 5

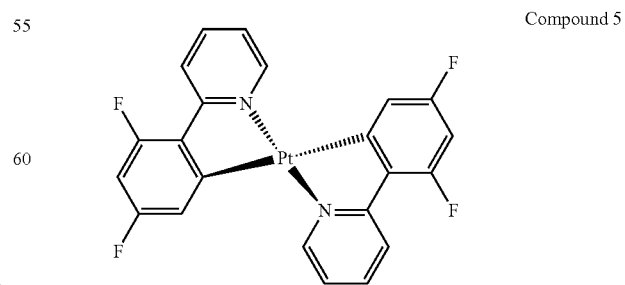

Compound 5

2.41 mmol (1 g) of potassium tetrachloroplatinate are suspended in 8 ml of degassed water with vigorous stirring. A solution of 5.3 mmol (1.013 g) of 2,4-di-fluorophenylpyridine in 24 ml of ethoxyethanol is added to this suspension. The suspension is heated to 80° C. for approx. 20 h, in the course of which a dark green precipitate increasingly forms. After cooling to room temperature, the crude product is precipitated by blanketing the suspension with 15 ml of water and stirring it after approx. 2 h. The crude product is filtered off with suction and washed repeatedly with a water/alcohol mixture (10:1). At this point, the product becomes air-stable. Subsequently, it is dried under reduced pressure for approx. 20 h.

Yield: 0.935 g (92%)

Compound 5 shows a mononuclear metal complex in which the central atom forms five-membered metallacyclic rings with the ligands.

Synthesis of di(μ-pyrazolato)bis[(phenylpyridino)-platinum(II)]=Compound 6

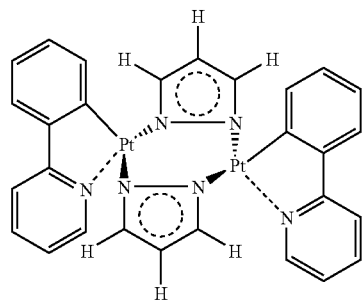

Compound 6

0.65 mmol (0.5 g) of di(μ-chloro)bis[(phenylpyridino)-platinum(II)] (compound 1) are suspended in 25 ml of dichloromethane. At the same time, 1.3 mmol (88.5 mg) of pyrazole and 1.3 mmol (70.23 mg) of sodium methoxide are likewise suspended in 15 ml of dichloromethane. Both suspensions are stirred for approx. 1 h, and then pyrazole suspension is added to the di(μ-chloro)bis[(phenylpyridino)platinum(II)] suspension. The mixture is stirred at room temperature for approx. 48 h. After 48 h, the mixture is filtered through a P4 frit and washed repeatedly with dichloromethane. The solution is concentrated under reduced pressure. Subsequently, the substance is washed twice with methanol and dried under reduced pressure.

Yield: 234 mg (43.3%)

Figure 3E:
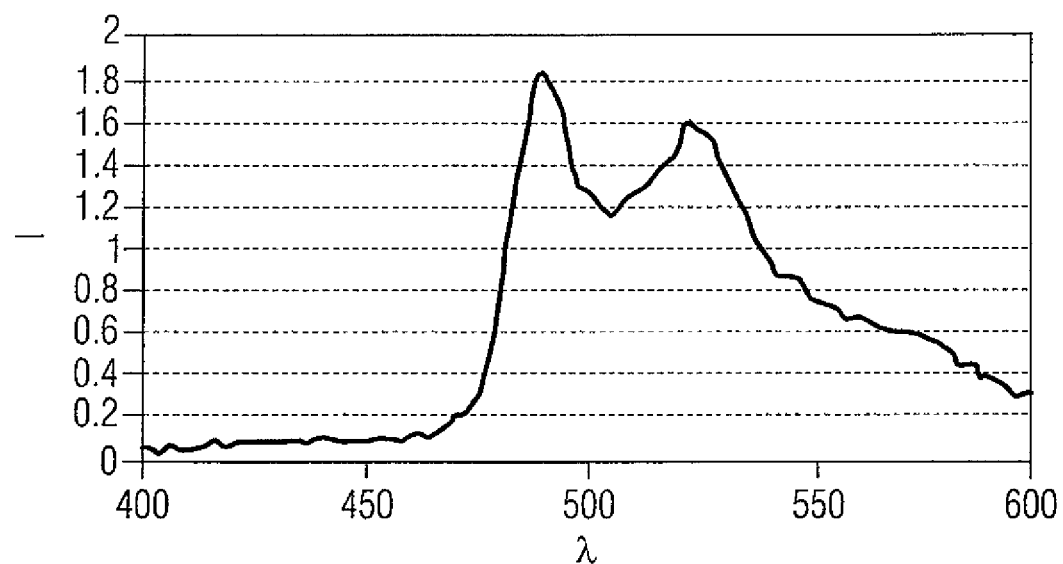

FIG. 3e shows the photoluminescence spectrum of the compound 6, with an emission maximum at 488 nm and 522 nm.

Synthesis of di(μ-pyrazolato)bis[(2,4-difluorophenyl-pyridino)platinum(II)]=Compound 7

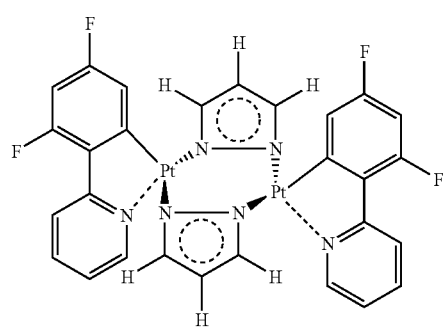

Compound 7

1.04 mmol (874 mg) of di(μ-chloro)bis[(2,4-difluoro-phenylpyridino)platinum(II)] (compound 2) are suspended in 10 ml of dichloromethane. A mixture of 2.078 mmol (112.2 mg) of sodium methoxide and 2.078 mmol (141.3 mg) of pyrazole, suspended in 40 ml of dichloro-methane, is slowly added dropwise thereto. The greenish reaction mixture is stirred at room temperature for 48 h. Subsequently, the mixture is filtered through a frit and washed through with dichloromethane. The filtrate is concentrated and the yellow product obtained is washed twice with hot methanol and once with pentane. Dry under reduced pressure.

Yield: 662 mg (71%)

Figure 3F:
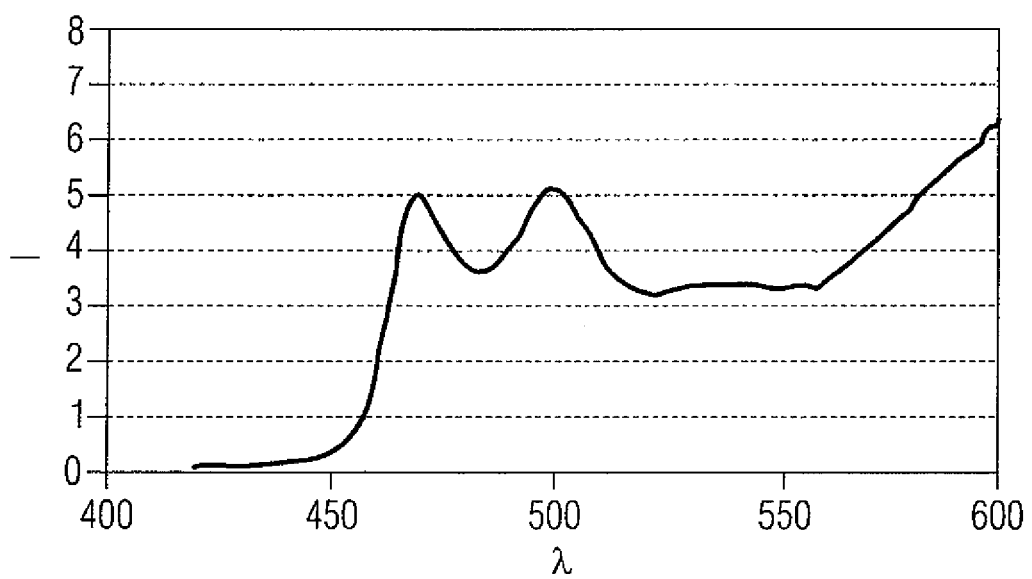

FIG. 3f shows the photoluminescence spectrum of compound 7, with an emission maximum at 470 nm and 501 nm.

Synthesis of di(μ-hpp)bis[(phenylpyridino)platinum(II)]=Compound 8

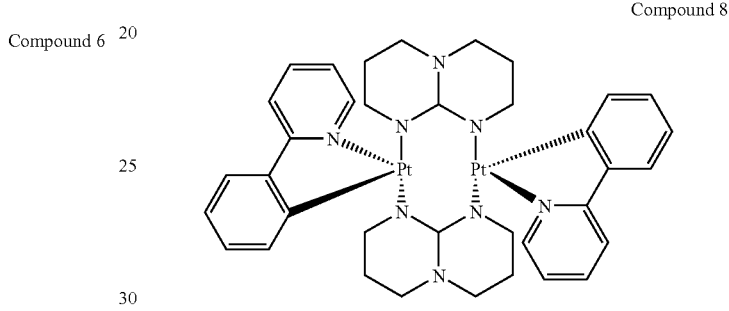

Compound 8

0.39 mmol (0.3 g) of di(g-chloro)bis[(phenylpyridino)-platinum(II)] (compound 1) are suspended in 25 ml of dichloromethane. At the same time, 0.78 mmol (108.6 mg) of Hhpp and 0.78 mmol (42.13 mg) of sodium methoxide are suspended in 20 ml of dichloromethane. Both suspensions are cooled to −70° C. with stirring, and then Hhpp suspension is added to the di(g-chloro)bis[(phenylpyridino)platinum(II)] suspension. The mixture is stirred at room temperature for approx. 48 h. After 48 h, the mixture is filtered through a P4 frit and washed through repeatedly with dichloro-methane. The solution is concentrated under reduced pressure. Subsequently, the substance is washed with pentane. However, the pentane extraction shows the same result in the photoluminescence spectrum as the washed product.

Yield: virtually quantitative

This compound can be detected by means of mass spectrometry.

Figure 3G:
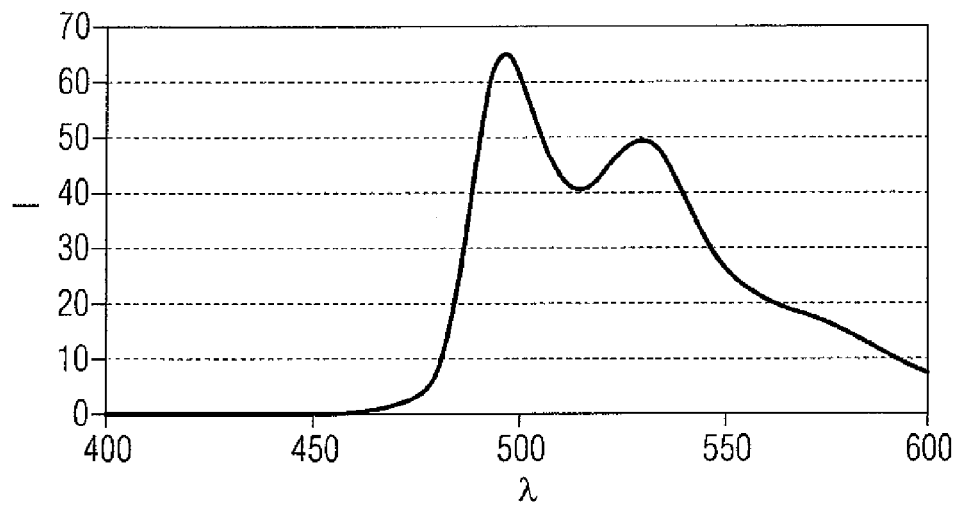

FIG. 3g shows the photoluminescence spectrum of compound 8, with an emission maximum at 498 nm and 531 nm.

Synthesis of di(μ-hpp)bis[(2,4-difluorophenyl-pyridine)platinum(II)]=Compound 9

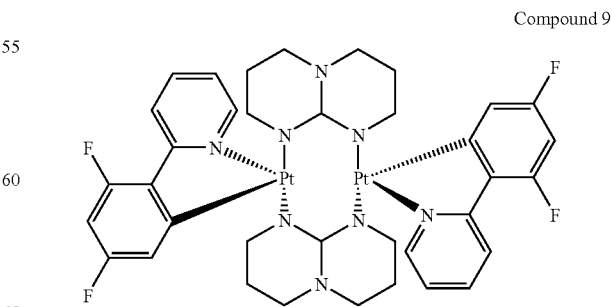

Compound 9

1.19 mmol (1 g) of di(g-chloro)bis[(2,4-difluorophenyl-pyridino)platinum(II)] (compound 2) are suspended in 20 ml of dichloromethane and cooled to −70° C. A mixture of 2.377 mmol (128.4 mg) of sodium methoxide and 2.377 mmol (330.9 mg) of Hhpp, suspended in 40 ml of dichloromethane and likewise cooled to −70° C., is slowly added dropwise thereto. The greenish reaction mixture is stirred at room temperature for 48 h, in the course of which the mixture turns brownish. Subsequently, it is filtered through a frit and washed through with di-chloromethane. The filtrate is concentrated to obtain a brownish-beige product. A fraction extracted with ether gives the same PL spectrum as the crude product.

Yield: virtually quantitative

Figure 3H:
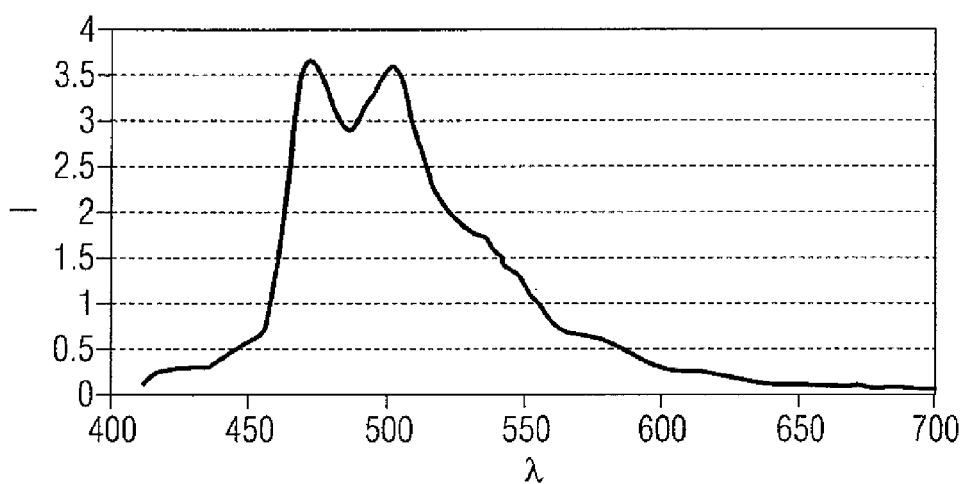

FIG. 3h shows the photoluminescence spectrum of compound 9, with an emission maximum at 473 nm and 501 nm.

Synthesis of di(μ-hpp)bis[(dipyridylamino)platinum (II)]=Compound 10

Compound 10

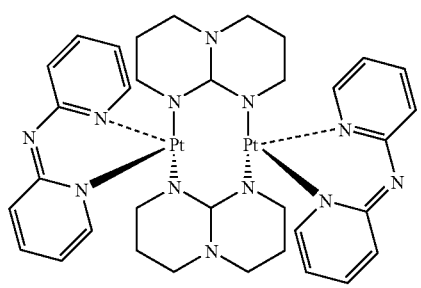

1.25 mmol (1 g) of di(μ-chloro)bis[(dipyridylamino)-platinum(II)] (compound 3) are suspended in 10 ml of dichloromethane and cooled to −70° C. A mixture of 2.496 mmol (134.8 mg) of sodium methoxide and 2.496 mmol (347.4 mg) of Hhpp, suspended in 35 ml of dichloromethane and likewise cooled to −70° C., is slowly added dropwise thereto. In the course of this, the reaction mixture turns yellow. The mixture is left to react at room temperature with stirring for 48 h. Thereafter, the substance is filtered through a P4 frit and washed through repeatedly with dichloromethane. The filtrate is concentrated and dried under reduced pressure.

Yield 1.04 g (83%)

This compound can be detected by means of mass spectrometry.

Figure 3I:
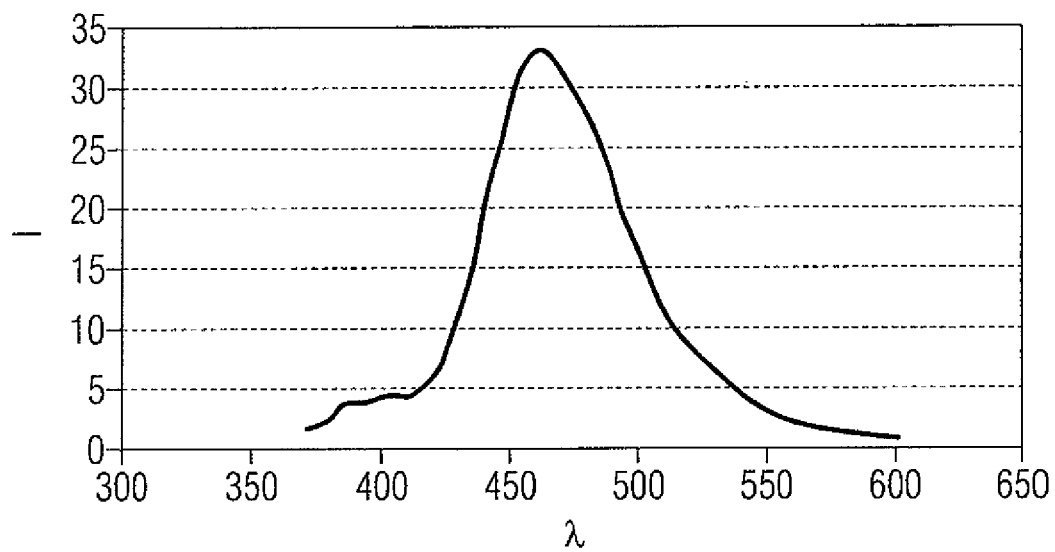

FIG. 3i shows the photoluminescence spectrum of compound 10, with an emission maximum at 463 nm.

Synthesis of di(μ-pyrazolato)bis[(dipyridylamino)-platinum(II)]=Compound 11

Compound 11

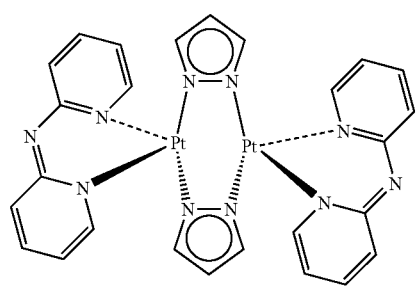

0.21 mmol (0.17 g) of di(μ-chloro)bis[(dipyridylamino)-platinum(II)] (compound 3) are suspended in 15 ml of dichloromethane. At the same time, 0.42 mmol (28.9 mg) of pyrazole and 0.42 mmol (22.9 mg) of sodium methoxide are suspended in 10 ml of dichloromethane. Both suspensions are stirred for approx. 1 h, and then the pyrazole suspension is added to the di(μ-chloro)bis[(dipyridylamino)platinum(II)] suspension. The mixture is stirred at room temperature for approx. 48 h. The color of the mixture is intense yellow. After 48 h, the substance is filtered through a P4 frit and washed through repeatedly with dichloromethane. The solution glows bright green under UV light (384 nm). It is subsequently dried under reduced pressure.

Yield: 0.03 g (16.4%)

Figure 3J:
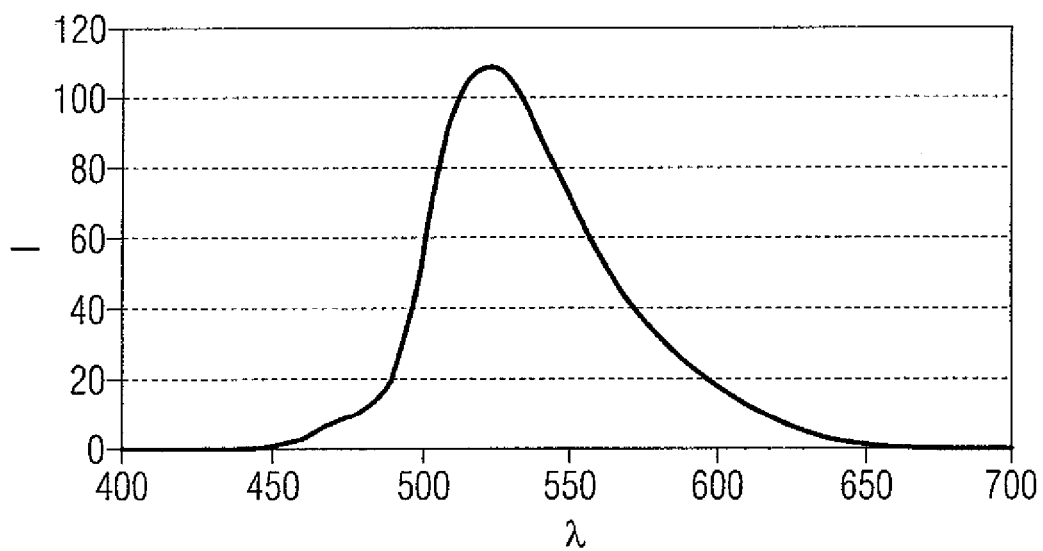

FIG. 3j shows the photoluminescence spectrum of compound 11, with an emission maximum at 524 nm.

According to the abovementioned synthesis methods, metal complexes of the formula 28 are also preparable.

Formula 28

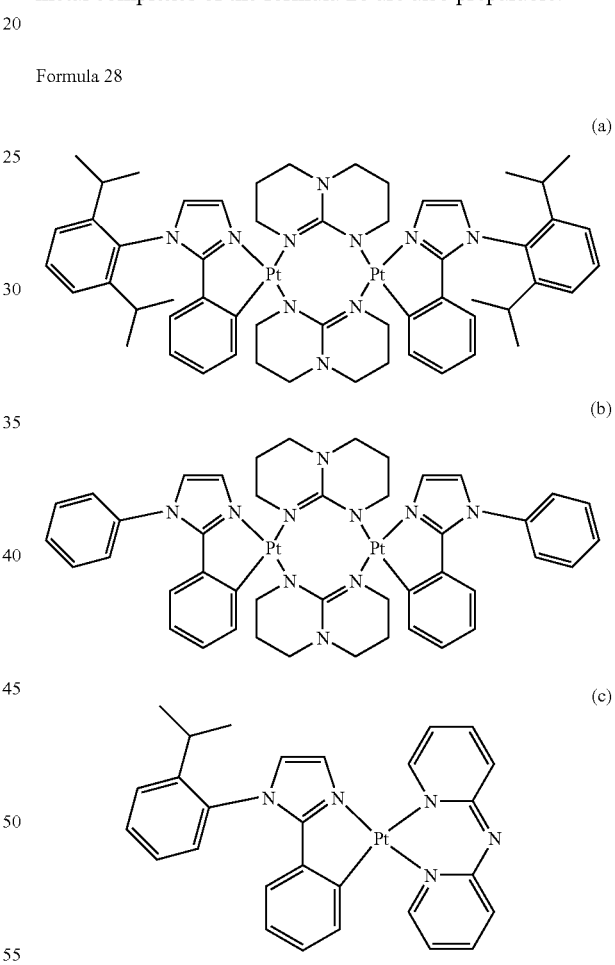

A further example of metal complexes is tris(dipyridylamine)iridium(III) (formula 29). This can be prepared, for example, as follows: dipyridylamine and iridium acetylacetonate are initially charged in glycol in a stoichiometric ratio and heated at reflux under inert gas for 12 h. Subsequently, the reaction mixture is admixed with water and the Ir derivative is extracted by means of chloroform. The chloroform phase is concentrated and then the product is precipitated by adding methanol.

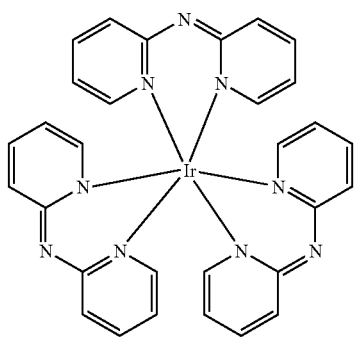

Formula 29

Figure 4A:
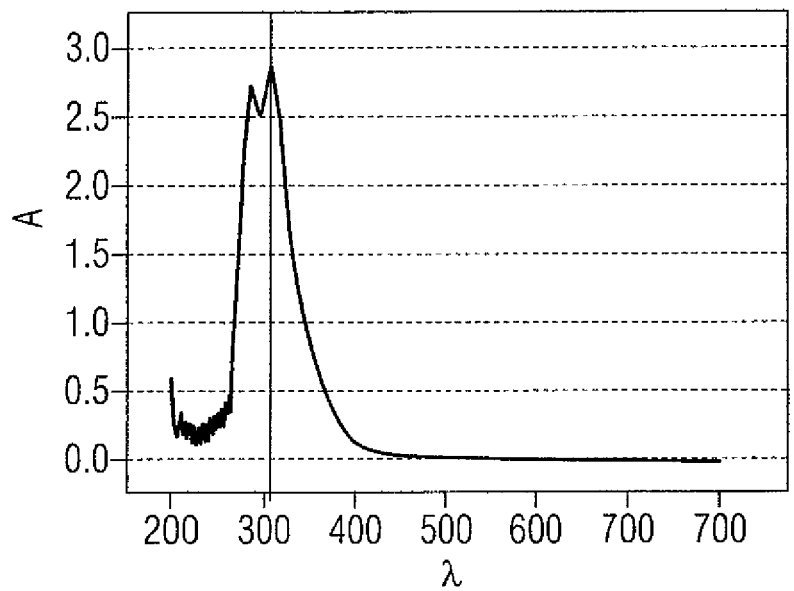
FIG. 4 shows a) the absorption spectrum and b) the photoluminescence emission spectrum of tris(dipyridyl-imine)iridium(III).

FIG. 4a shows the absorption spectrum (absorption A against wavelength λ in nm) of tris(dipyridyl-imine)iridium (III). A double peak is evident around 300 nm.

Figure 4B:
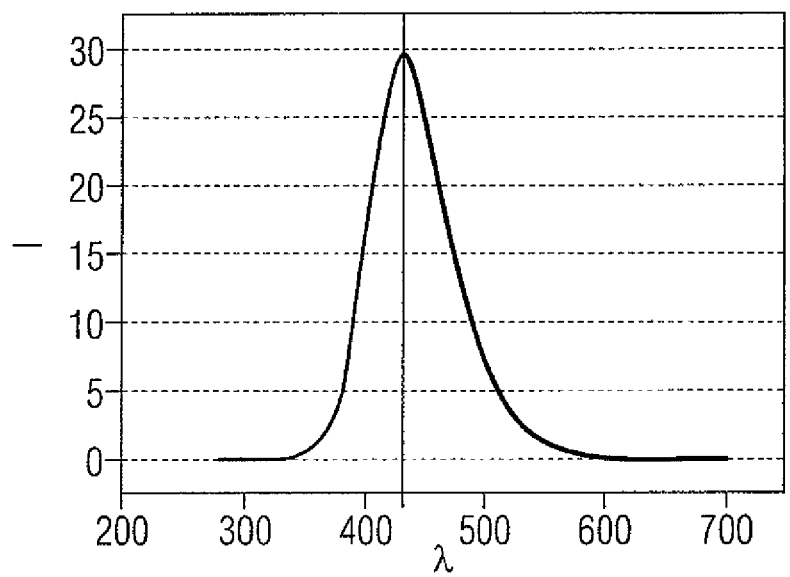

FIG. 4b shows the PL emission spectrum (intensity I against wavelength λ in nm) of the tris(dipyridyl-imine)iridium(III) complex. A single peak is evident at approx. 430 nm.

A further example of a metal complex is tris(di-1,2,4-benzotriazin-3-ylmethine)iridium(III) (formula 30), which can be prepared as follows: dibenzo-1,2,4-triazin-3-ylmethane and iridium acetylacetonate are initially charged in a stoichiometric ratio in glycol and heated at reflux under inert gas for 15 h. Subsequently, the reaction mixture is admixed with water and the Ir derivative is extracted by means of chloroform. The chloroform phase is concentrated and then the product is precipitated by adding methanol.

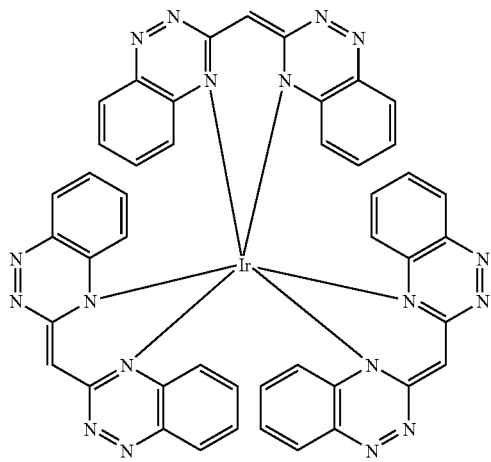

Formula 30

Figure 5A:
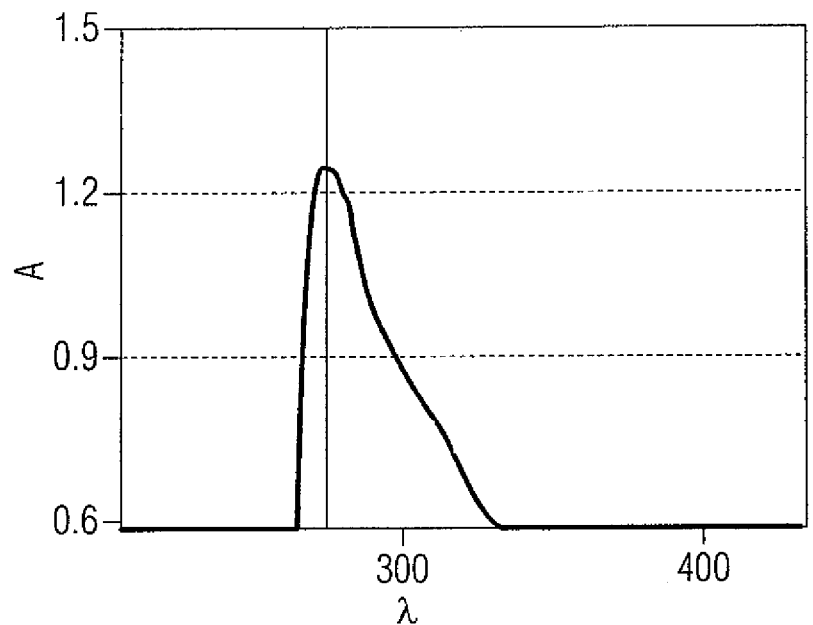
FIG. 5 shows a) the absorption spectrum and b) the photoluminescence emission spectrum of tris(di-1,2,4-benzotriazin-3-ylmethine)iridium(III).

FIG. 5a shows the absorption spectrum (absorption A against wavelength λ in nm) of tris(di-1,2,4-benzo-triazin-3-ylmethine)iridium(III). A peak is evident at approx. 280 nm.

Figure 5B:
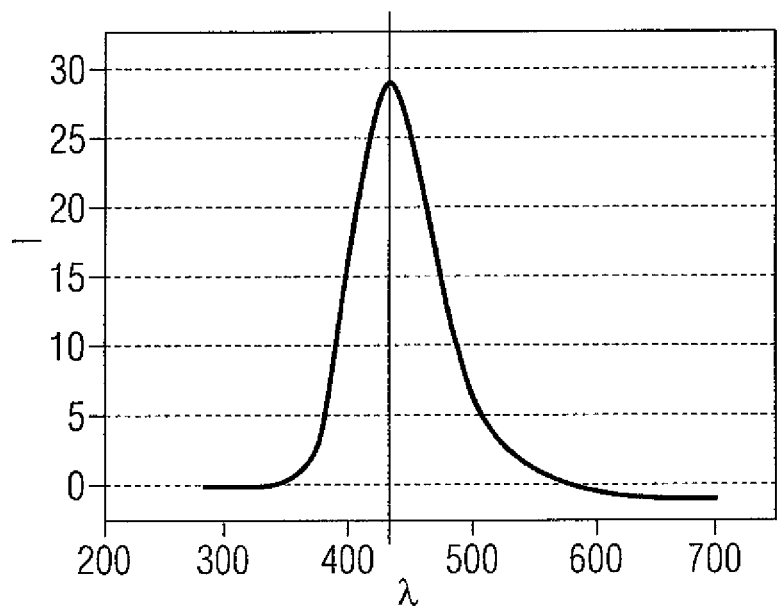

FIG. 5b, finally, shows a PL emission spectrum (intensity I against wavelength λ in nm) of the tris(di-1,2,4-benzotriazin-3-ylmethine)iridium(III) complex; a peak is evident at approx. 420 nm.

The embodiments shown in FIGS. 1 to 5 and the working examples can be varied as desired. It should also be taken into account that the invention is not restricted to the examples, but permits further configurations not detailed here.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A phosphorescent metal complex which comprises at least one metallic central atom M and at least one bidentate ligand coordinated by the metallic central atom M, wherein the one metallic central atom M and the bidentate ligand form a six-membered metallacyclic ring, wherein
    the bidentate ligand which forms a six-membered metallacyclic ring with the metallic central atom has a tautomerizable unit in the uncoordinated state,
    the metallic central atom M is selected from a group which comprises Ir, Pt, Au, Re, Rh, Ru, Os, Pd, Ag, Zn, Al and lanthanoids,
    the six-membered metallacyclic ring has a structural formula selected from the group which comprises

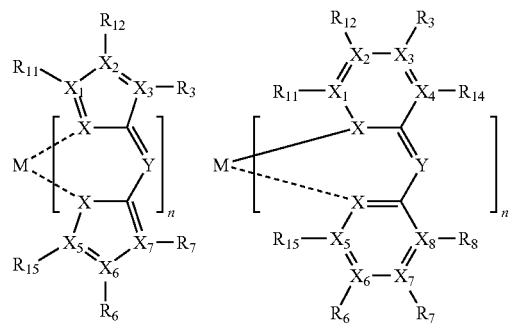

where:
n=1 to 3,
Y=C—H, N, P, As, Sb, C—$R_y$, Si—$R_y$, Ge—$R_y$,
X=O, P, As, Sb,
$X_1, X_2, X_3, X_4, X_5, X_6, X_7$ and $X_8$ are each independently C or — when $R_{11}, R_{12}, R_3, R_{14}, R_{15}, R_6, R_7$ or $R_8$ includes a free electron pair —N,
$R_y, R_{11}, R_{12}, R_3, R_{14}, R_{15}, R_6, R_7, R_8$ are each independently H, unbranched alkyl radicals, branched alkyl radicals, fused alkyl radicals, cyclic alkyl radicals, fully or partly substituted unbranched alkyl radicals, fully or partly substituted branched alkyl radicals, fully or partly substituted fused alkyl radicals, fully or partly substituted cyclic alkyl radicals, alkoxy groups, amines, amides, esters, carbonates, aromatics, fully or partly substituted aromatics, fused aromatics, fully or partly substituted fused aromatics, heterocycles, fully or partly substituted heterocycles, fused heterocycles, fully or partly substituted heterocycles, F and CN.

2. A radiation-emitting component comprising:
a substrate;
a first electrode layer on the substrate;
at least one organic emitting layer on the first electrode layer; and
a second electrode layer on the organic emitting layer,
wherein the organic emitting layer comprises a phosphorescent metal complex as claimed in claim 1.

* * * * *